United States Patent
Ron et al.

(10) Patent No.: US 7,838,024 B2
(45) Date of Patent: Nov. 23, 2010

(54) METHODS AND DEVICES FOR THE SUSTAINED RELEASE OF MULTIPLE DRUGS

(75) Inventors: Eyal S. Ron, Lexington, MA (US); Robert S. Langer, Newton, MA (US); William F. Crowley, Jr., Newtonville, MA (US)

(73) Assignees: The General Hospital Corporation, Boston, MA (US); Massachusetts Institute of Technology, Boston, MA (US)

( * ) Notice: Subject to any disclaimer, the term of this patent is extended or adjusted under 35 U.S.C. 154(b) by 0 days.

(21) Appl. No.: 12/125,571

(22) Filed: May 22, 2008

(65) Prior Publication Data
US 2008/0248017 A1    Oct. 9, 2008

Related U.S. Application Data

(62) Division of application No. 10/835,414, filed on Apr. 29, 2004.

(60) Provisional application No. 60/466,318, filed on Apr. 29, 2003, provisional application No. 60/473,579, filed on May 27, 2003.

(51) Int. Cl.
*A61F 6/14* (2006.01)
*A61F 6/06* (2006.01)

(52) U.S. Cl. .................. 424/432; 128/833; 514/843

(58) Field of Classification Search .............. None
See application file for complete search history.

(56) References Cited

U.S. PATENT DOCUMENTS

| 3,454,004 | A | * | 7/1969 | Spencer et al. ............ 128/839 |
| 3,527,210 | A | * | 9/1970 | Towns ..................... 128/839 |
| 3,545,439 | A | | 12/1970 | Duncan |
| 3,624,203 | A | | 11/1971 | Overbeek et al. |
| 3,708,511 | A | | 1/1973 | Van Vliet et al. |
| 3,780,935 | A | | 12/1973 | Lukacs et al. |
| 3,880,759 | A | | 4/1975 | Van Assendelft |
| 3,892,664 | A | | 7/1975 | Van Assendelft et al. |

(Continued)

FOREIGN PATENT DOCUMENTS

EP    0 121 275    10/1984

(Continued)

OTHER PUBLICATIONS

Merriam-Webster Online Medical Dictionary; term searched: estrogen.*

(Continued)

*Primary Examiner*—Robert A Wax
*Assistant Examiner*—Jeffrey T Palenik
(74) *Attorney, Agent, or Firm*—Nutter McClennen & Fish LLP

(57) ABSTRACT

The invention relates to an drug delivery device and a method for delivering multiple drugs over a prolonged period of time. The drug delivery device has two or more unitary segments comprising a drug-permeable polymeric substance, wherein at least one of the segments further comprises a pharmaceutically active agent. The invention also relates to a method for the treatment of a benign ovarian secretory disorder in a female mammal, a method of contraception, and a method of relieving the symptoms associated with menopausal, peri-menopausal and post-menopausal periods in a woman.

9 Claims, 9 Drawing Sheets

U.S. PATENT DOCUMENTS

| | | | |
|---|---|---|---|
| 3,903,880 A * | 9/1975 | Higuchi et al. | 128/833 |
| 3,920,805 A | 11/1975 | Roseman | |
| 3,938,515 A | 2/1976 | Leeper et al. | |
| 3,963,119 A | 6/1976 | Lukacs et al. | |
| 3,995,633 A | 12/1976 | Gougeon | |
| 3,995,634 A | 12/1976 | Drobish | |
| 4,016,251 A * | 4/1977 | Higuchi et al. | 424/432 |
| 4,043,928 A | 8/1977 | Lukacs et al. | |
| 4,069,307 A * | 1/1978 | Higuchi et al. | 424/432 |
| 4,093,709 A | 6/1978 | Choi et al. | |
| 4,096,860 A | 6/1978 | McLaughlin | |
| 4,144,317 A * | 3/1979 | Higuchi et al. | 424/435 |
| 4,155,991 A * | 5/1979 | Schopflin et al. | 424/432 |
| 4,219,426 A | 8/1980 | Spekle et al. | |
| 4,237,885 A | 12/1980 | Wong et al. | |
| 4,292,965 A | 10/1981 | Nash et al. | |
| 4,484,599 A | 11/1984 | Hanover et al. | |
| 4,525,340 A | 6/1985 | Lange et al. | |
| 4,558,996 A | 12/1985 | Becker | |
| 4,596,576 A * | 6/1986 | de Nijs | 424/432 |
| 4,629,449 A | 12/1986 | Wong | |
| 4,645,502 A | 2/1987 | Gale et al. | |
| 4,822,616 A | 4/1989 | Zimmermann et al. | |
| 4,871,543 A | 10/1989 | Lindskog et al. | |
| 4,897,200 A | 1/1990 | Smakman et al. | |
| 4,938,759 A | 7/1990 | Enscore et al. | |
| 4,957,119 A | 9/1990 | de Nijs et al. | |
| 5,002,540 A | 3/1991 | Brodman et al. | |
| 5,088,505 A | 2/1992 | De Nijs et al. | |
| 5,150,718 A | 9/1992 | De Nijs et al. | |
| 5,211,952 A | 5/1993 | Spicer et al. | |
| 5,302,397 A * | 4/1994 | Amsden et al. | 424/473 |
| 5,324,523 A | 6/1994 | Zsuga et al. | |
| 5,340,584 A | 8/1994 | Spicer et al. | |
| 5,340,585 A | 8/1994 | Pike et al. | |
| 5,476,652 A | 12/1995 | Chinuki et al. | |
| 5,482,706 A | 1/1996 | Igari et al. | |
| 5,543,150 A | 8/1996 | Bologna et al. | |
| 5,593,965 A | 1/1997 | Lovas et al. | |
| 5,601,839 A | 2/1997 | Quan et al. | |
| 5,605,702 A | 2/1997 | Teillaud et al. | |
| 5,681,568 A | 10/1997 | Goldin et al. | |
| 5,725,852 A | 3/1998 | Igari et al. | |
| 5,738,864 A | 4/1998 | Schacht et al. | |
| 5,807,574 A * | 9/1998 | Cheskin et al. | 424/451 |
| 5,834,010 A | 11/1998 | Quan et al. | |
| 5,840,685 A | 11/1998 | Fujii et al. | |
| 5,855,906 A | 1/1999 | McClay et al. | |
| 5,869,081 A | 2/1999 | Jackanicz et al. | |
| 5,919,478 A | 7/1999 | Landrau et al. | |
| 5,941,844 A | 8/1999 | Eckenhoff | |
| 5,945,123 A | 8/1999 | Hermelin | |
| 5,958,446 A | 9/1999 | Miranda et al. | |
| 5,972,372 A | 10/1999 | Saleh et al. | |
| 5,985,861 A | 11/1999 | Levine et al. | |
| 5,989,581 A | 11/1999 | Groenewegen et al. | |
| 6,001,390 A | 12/1999 | Yum et al. | |
| 6,013,276 A | 1/2000 | Math et al. | |
| 6,013,853 A | 1/2000 | Athanasiou et al. | |
| 6,039,968 A | 3/2000 | Nabahi et al. | |
| 6,068,909 A | 5/2000 | Koseki et al. | |
| 6,083,916 A | 7/2000 | Nonomura et al. | |
| 6,086,909 A | 7/2000 | Harrison et al. | |
| 6,103,256 A | 8/2000 | Nabahi et al. | |
| 6,113,938 A | 9/2000 | Chen et al. | |
| 6,113,943 A | 9/2000 | Okada et al. | |
| 6,126,958 A | 10/2000 | Saleh et al. | |
| 6,139,873 A | 10/2000 | Hughes, Jr. et al. | |
| 6,143,314 A | 11/2000 | Chandrashekar et al. | |
| 6,149,935 A | 11/2000 | Chiang et al. | |
| 6,156,331 A | 12/2000 | Peery et al. | |
| 6,159,490 A | 12/2000 | Deghenghi et al. | |
| 6,159,491 A | 12/2000 | Durrani | |
| 6,180,129 B1 | 1/2001 | Magruder et al. | |
| 6,180,608 B1 | 1/2001 | Gefter et al. | |
| 6,180,609 B1 | 1/2001 | Garnick et al. | |
| 6,197,327 B1 | 3/2001 | Harrison et al. | |
| 6,217,893 B1 | 4/2001 | Pellet et al. | |
| 6,218,367 B1 | 4/2001 | Jacob | |
| D442,688 S | 5/2001 | DeWeerd et al. | |
| 6,264,973 B1 | 7/2001 | Mahashabde et al. | |
| 6,264,981 B1 | 7/2001 | Zhang et al. | |
| 6,394,094 B1 | 5/2002 | McKenna et al. | |
| 6,416,779 B1 | 7/2002 | D'Augustine et al. | |
| 6,544,546 B1 * | 4/2003 | Groenewegen et al. | 424/432 |
| 6,572,874 B1 | 6/2003 | Harrison et al. | |
| 6,905,701 B2 | 6/2005 | Pauletti et al. | |
| 2003/0049311 A1 * | 3/2003 | McAllister et al. | 424/452 |

FOREIGN PATENT DOCUMENTS

| | | |
|---|---|---|
| EP | 0 259 136 | 3/1988 |
| EP | 0 285 057 | 10/1988 |
| EP | 0 302 693 | 2/1989 |
| EP | 0 303 306 | 2/1989 |
| EP | 0 503 521 | 9/1992 |
| EP | 0 737 477 | 10/1996 |
| EP | 0 876 815 | 11/1998 |
| EP | 0887074 A2 | 12/1998 |
| EP | 0 940 678 | 9/1999 |
| EP | 1 142 959 | 10/2001 |
| EP | 1 221 315 | 7/2002 |
| JP | 51-064793 A | 6/1976 |
| JP | 61-106508 A | 5/1986 |
| JP | 01-502265 T | 8/1989 |
| JP | 10510168 T | 10/1998 |
| JP | 11-009699 A | 1/1999 |
| JP | 11-512965 T | 11/1999 |
| JP | 2002-513690 T | 5/2002 |
| JP | 2003507109 T | 2/2003 |
| WO | 87/05514 | 9/1987 |
| WO | 89/07959 | 9/1989 |
| WO | 91/06290 | 5/1991 |
| WO | 92/05776 | 4/1992 |
| WO | 92/16836 | 10/1992 |
| WO | 93/00058 | 1/1993 |
| WO | 93/09765 | 5/1993 |
| WO | 95/01979 | 1/1995 |
| WO | 95/05200 | 2/1995 |
| WO | 95/33747 | 12/1995 |
| WO | 96/01092 A1 | 1/1996 |
| WO | 96/05315 | 2/1996 |
| WO | 96/31197 | 10/1996 |
| WO | 96/33678 | 10/1996 |
| WO | 96/34597 | 11/1996 |
| WO | 96/40139 | 12/1996 |
| WO | 97/02015 | 1/1997 |
| WO | WO 97/02015 * | 1/1997 |
| WO | 98/04220 A1 | 2/1998 |
| WO | 98/26788 | 6/1998 |
| WO | 98/39042 | 9/1998 |
| WO | 99/24086 | 5/1999 |
| WO | 99/30976 | 6/1999 |
| WO | 99/56934 | 11/1999 |
| WO | 00/00158 | 1/2000 |
| WO | 00/01687 | 1/2000 |
| WO | 00/34255 | 6/2000 |
| WO | 00/41704 | 7/2000 |
| WO | 00/59512 | 10/2000 |
| WO | 00/74742 | 12/2000 |
| WO | 01/13780 A2 | 3/2001 |
| WO | 01/34201 | 5/2001 |
| WO | 01/59109 | 8/2001 |
| WO | 01/59118 | 8/2001 |

| | | |
|---|---|---|
| WO | 01/64161 | 9/2001 |
| WO | 01/81408 | 11/2001 |
| WO | 01/85257 | 11/2001 |
| WO | 02/34311 | 5/2002 |
| WO | 0240001 | 5/2002 |

OTHER PUBLICATIONS www.caymanchem.com (see attached pdf for norgestrel and ethynylestradiol).*
http://en.wikipedia.org/wiki/Torus.*
Glasier, Anna; Expert Opinion on Investigational Drugs (2002) 11(9): 1239-1251.*
Roumen et al. Contraception, 59 (1) pp. 59-62 (1999).*
Roumen et al. "Clinical Acceptability of an Ethylene-Vinyl-Acetate Nonmedicated Vaginal Ring"; Contraception 1999; 59:59-62.*
U.S. Patent Documents -- None.*
Non-Patent Literature Documents -- None.*
EP 04 76 0436 (PCT/US2004/013172), Supplementary European Search Report, issued Oct. 17, 2007 (5 pages).
EP 04 76 0436 (PCT/US2004/013172), Supplementary Partial European Search Report, issued Aug. 20, 2007 (5 pages).
Bernkop-Schnurch et al, "Intravaginal Drug Delivery Systems", Am. J. Drug Deliv, 1(4), pp. 241-254 (2003).
Johansson et al., "New Delivery Systems in Contraception: Vaginal Rings", American Journal of Obstetrics and Gynecology, 190, s54-9 (2004).

* cited by examiner

METHODS AND DEVICES FOR THE SUSTAINED RELEASE OF MULTIPLE DRUGS

RELATED APPLICATION(S)

This application is a divisional application of U.S. patent application Ser. No. 10/835,414, filed on Apr. 29, 2004, entitled "Methods and Devices for the Sustained Release of Multiple Drugs," which claims the benefit of U.S. Provisional Application No. 60/466,318, filed on Apr. 29, 2003 and U.S. Provisional Application No. 60/473,579, filed on May 27, 2003. The entire teachings of the above applications are incorporated herein by reference.

FIELD

The invention relates to drug delivery devices for the simultaneous release of multiple drugs in a substantially constant ratio over a prolonged period of time. More specifically the invention relates to intravaginal devices and methods for contraception, hormone replacement therapy, and therapeutic methods for the treatment of reproductive conditions and disorders, such as benign ovarian secretory disorders.

BACKGROUND

The desirability of sustained release drug formulations has long been a goal in the pharmaceutical industry. Sustained release systems solve many of the problems associated with conventional drug delivery systems, e.g., pills. For example in conventional drug delivery systems administration of the drug is given frequently and results in high variability in circulating drug levels during the course of treatment. The concentration of the drug increases to therapeutic concentrations after administration, but in some instances the concentration rises above the minimal therapeutic level reaching the toxic threshold. After a relatively short period of the drug concentration decreases via metabolization or excretion to levels that are no longer therapeutic.

In order to achieve constant levels of drugs and avoid the inefficiencies of the drug concentration peaks and valleys the drugs should be released from a delivery system at a rate that does not change with time (so called zero-order release). Preferably, the initial dose of a drug is the therapeutic dose, which is maintained by the delivery system. Examples of a current sustained drug delivery system include the reservoir systems which consist of tubes, fibers, laminates, or microspheres. In these systems, a drug reservoir is coated in a rate-controlling membrane. Drug diffusion across the membrane is rate limiting and is constant (zero order) as long as the membrane's permeability does not change and as long as the concentration of drug in the reservoir is constant.

In matrix systems drugs are dispersed through a matrix and are released as the drugs dissolve and diffuse through the matrix. A drug is released from the outer surface of the matrix first, this layer becomes depleted, and a drug that is released from further within the core of the device must then diffuse through the depleted matrix. The net result is that the release rate slows down and thus it is very difficult to maintain constant and consistent release. Other types of devices are polymeric devices that contain a polymeric material that is permeable to the passage of the drug. Although it is possible to choose from among a large variety of polymeric materials, in practice only a small number of polymers have been shown to function satisfactorily as a release-determining outer layer of the reservoir. Sustained release systems that release two or more active substances over a prolonged period of time are extremely useful for certain applications, for example, the in fields of contraception and hormone replacement therapy.

Ring-shaped vaginal drug delivery devices ("vaginal rings") are well known in the art. Such devices are designed to deliver a relatively constant dose of drug to the vagina, usually over a period of weeks to months. Typically, they are made of a silicone elastomer and contain a drug released by diffusion though the elastomer. Vaginal rings have been developed for delivering steroids to treat post-menopausal vaginal conditions, as well as for contraception and hormone replacement therapy. Women generally prefer vaginal rings to oral delivery for several reasons, particularly their convenience, privacy, long-term delivery capacity, and effectiveness. Vaginal rings provide a regulated dose of drug with minimal involvement or attention by the user. They also avoid the first pass of orally administered drugs through the liver, where appreciable portions of the daily dosage of some orally administered steroids are degraded.

U.S. Pat. No. 4,292,965 (Nash et al.) and U.S. Pat. No. 4,822,616 (Zimmermann et al.) disclose two-layered vaginal rings. The rings comprise an inner drug-free supporting ring, a middle layer comprising a drug, and an outer drug-free layer. All three layers preferably comprise a silicone elastomer. However, the use of silicone elastomers is now generally considered to be unsafe, and is no longer the material of choice.

In addition to single drug delivery, vaginal rings have been developed for simultaneous release of multiple drugs over a prolonged period of time. For example, U.S. Pat. No. 3,995,633 (Gougeon) and U.S. Pat. No. 3,995,634 (Drobish) disclose vaginal rings comprising separate reservoirs containing different active substances, wherein the reservoirs are arranged in holders. U.S. Pat. No. 4,237,885 (Wong et al.) also discloses a multi-reservoir device, in which spacers are used to divide a tube or coil into portions, wherein each portion is filled with a different active substance in a silicone fluid and the two ends of the tube are subsequently connected to form a ring. Patent Publication WO 97/02015 (Groenewegen et al.) discloses a two-compartment device, wherein one compartment has a core, a medicated middle layer and a non-medicated outer layer, and a second compartment having a medicated core and a non-medicated outer layer. However, the active substances in these multi-compartment or multi-reservoir devices typically diffuse through the walls of the tubes, thus allowing drug interactions, particularly during prolonged storage. Interactions between the drugs often results in degradation or inactivation of at least one of the drugs, and thus variations in the pre-set fixed release ratio between the drugs over time.

The device described in U.S. Pat. No. 4,596,576 (de Nijs) was designed to overcome the diffusion problem associated with multi-compartment devices. de Nijs discloses a two-compartment vaginal ring wherein each compartment comprises a reservoir filled with a different active substance. However, to prevent diffusion and maintain a constant release ratio between the various active substances over time, the drug compartments are separated by impermeable inert stoppers, formed of glass, gold or silver. Although the stoppers effectively prevent diffusion of active substance between reservoirs, the device is complicated and expensive to manufacture.

The device described in U.S. Pat. No. 5,989,581 (Groenewegen) was also designed to overcome the diffusion problems associated with existing delivery systems, as well as to provide a less complicated and cheaper device for intravaginal delivery of multiple active substances. The patent discloses a ring-shaped drug delivery system for the simultaneous release of a progestogenic steroid compound and an estrogenic steroid compound, reportedly in a fixed ratio over a prolonged period of time. The drug delivery system has a compartment comprising a thermoplastic polymer core containing the mixture of the progestogenic and estrogenic compounds and a thermoplastic polymer skin. However, like other known vaginal devices, the Groenewegen device suffers from its own inherent limitations. In general, the release per unit time of a drug is determined by the solubility of the active substance in the outer layer (wall) of polymeric material and by the diffusion coefficient of the active substance in the wall. Thus, the choice of the outer layer material of the reservoir largely determines the release ratio of the active substances contained in the reservoir. Unfortunately, only a few polymers are capable of functioning satisfactorily as a release-determining outer layer of the reservoir. Finding the appropriate polymer for a particular drug or drug combination can be difficult. Moreover, the reservoir material must be capable of taking up a large amount of the active substance or substances in order to provide an adequate supply of the substances to the outer wall. Meeting these challenges is problematic, if not impossible, and must be addressed for each new drug or drug combination.

An intravaginal drug delivery device which can release two or more active substances in a substantially constant ratio to one another over a lengthy period of time would be extremely useful for certain applications. For example, in the field of contraception and in the field of hormone replacement therapy, extensive use is made of the simultaneous administration of an agent having a progestogenic activity and an agent having an estrogenic activity, preferably in a substantially constant ratio.

Drug delivery systems and methods for contraception and for treating female reproductive disorders using combination therapy have been developed. For example, U.S. Pat. No. 4,762,717 (Crowley, Jr.) discloses a delivery system for the continuous delivery of LHRH compositions in combination with sex steroid for use as a contraceptive. U.S. Pat. No. 5,130,137 (Crowley, Jr.) discloses a similar delivery system for the treatment of benign ovarian secretory disorders.

Despite these significant advances in the field, a need exists for an improved method for contraception and treatment of female reproductive conditions and disorders, such as treatment of benign ovarian secretory disorders and post-menopausal hormone replacement therapy. In particular, a method that uses a hormone replacement steroid and/or a LHRH and/or its analogues (either agonists and/or antagonists), and that can be administered in a safe, physiologic, and convenient manner, would be highly desirable. Moreover, a need exists for an improved drug delivery system for the simultaneous release of LHRH and sex steroids or sex steroid modulators, particularly a system which releases the LHRH and steroids in a substantially constant ratio over a prolonged period of time, and which is easy and inexpensive to manufacture.

Additionally, constant and reliable delivery of drugs or combinations of drugs over long periods of time would be useful in a wide variety of applications, including treatment or prevention of AIDS/HIV, atherosclerosis, various cancers, cardiovascular diseases, hypertension, toxemia of pregnancy, seizures, degenerative neurological disorders, diabetes, hematological disorders, addictions, and obesity and eating disorders, to name a few. Unfortunately, in addition to not always providing satisfactory release, release ratio, or release term in some cases, all currently available intravaginal drug delivery devices suffer from being relatively complicated, making them expensive to manufacture. Thus, a need exists for an improved drug delivery device for the simultaneous release of multiple drugs, particularly a device which releases the drugs in a substantially constant ratio over a prolonged period of time, and which is easy and inexpensive to manufacture.

SUMMARY

It is an object of the present invention to provide a drug delivery device for the sustained release of multiple drugs over a prolonged period of time. Additionally, the present invention also provides for a less expensive and easier to produce device than currently available devices. It is also an object of the invention to provide a method of treating disease with the device, particularly benign ovarian secretory disorders. It is also an object of the invention to administer multiple drugs for use in contraception and hormone replacement therapy.

In a first aspect, the present invention relates to a drug delivery device comprising two or more unitary segments. Each segment comprises a drug-permeable polymeric substance, and at least one segment comprises a mixture of the drug-permeable polymeric substance and a drug. Two or more segments may each contain a drug, preferably a different drug in each segment. The drug-permeable polymeric substance may be a thermoplastic polymer, such as an ethylene-vinyl acetate copolymer. At least one end of a segment may be attached to the end of another unitary segment by a coupling means, such as an adhesive material or by annealing the ends of the segments to same or different thermoplastic polymers. The drug delivery device may be in the shape of a ring, a wafer, or a suppository, and may be suitable for use as a vaginal ring. The drug delivery device may have an overall diameter of from 40 mm to 80 mm, and a cross-sectional diameter of from 2 mm to 12 mm. The drug to be delivered may be a hormone replacement steroid or a contraceptive agent, for example an estrogenic compound, a progestational compound, and/or a gonadotropin releasing hormone or its peptide or non-peptide agonists or antagonist analogues. The drug may also be an interferon, anti-angiogenesis factors, growth factors, hormones, enzymes, transferases, hydrolases, lysases, isomerases, proteases, ligases and oxidoreductases, enzyme inhibitors, steroids, anti-cancer drugs, antibiotics, growth hormone, polysaccharides, antigens, and antibodies.

In another aspect, the invention relates to a drug delivery system for the simultaneous release of two or more drugs. The drug delivery system comprises two or more unitary segments, wherein at least two of the segments comprise a mixture of a drug-permeable polymeric substance and a drug. Moreover, at least two of the segments may comprise a different drug, and the drug-permeable polymeric substance may be a thermoplastic polymer, such has an ethylene-vinyl acetate copolymer. The drug may be a hormone replacement steroid or a contraceptive agent, for example an estrogenic compound, a progestational compound, and/or a gonadotropin releasing hormone or its agonistic or antagonistic analogues. The drug may also be an interferon, anti-angiogenesis factors, growth factors, hormones, enzymes, transferases, hydrolases, lysases, isomerases, proteases, ligases and oxidoreductases, enzyme inhibitors, steroids, anti-cancer drugs, antibiotics, growth hormone, polysaccharides, antigens, and antibodies.

In still a further aspect, the invention relates to a method for delivering a drug to a female mammal. The method comprises preparing a drug delivery device comprising two or more unitary segments, wherein each segment comprises a drug-permeable polymeric substance, and wherein at least one segment comprises a mixture of the drug-permeable polymeric substance and a drug. The drug delivery device is then positioned in the vaginal tract of the female mammal, and maintained in the vaginal tract for a period of time sufficient to deliver an effective amount of the drug to the female mammal. The drug-permeable polymeric substance may be a thermoplastic polymer, such as an ethylene-vinyl acetate copolymer. The drug may be a hormone replacement steroid or a contraceptive agent, for example an estrogenic compound, a progestational compound, and/or a gonadotropin releasing hormone. The drug may also be interferon, anti-angiogenesis factors, growth factors, hormones, enzymes, transferases, hydrolases, lysases, isomerases, proteases, ligases and oxidoreductases, enzyme inhibitors, steroids, anti-cancer drugs, antibiotics, growth hormone, polysaccharides, antigens, and antibodies. In yet another aspect, the invention relates to a method of making a ring-shaped drug delivery device. The method comprises mixing a first drug-permeable polymeric substance with a first drug to form a first polymeric mixture, molding the first polymeric mixture to form a first ring, and cutting the first ring to form two or more first unitary segments. The method is then repeated with a second drug-permeable polymeric substance and a second drug to form a second unitary segment. The first and second drug-permeable polymeric substances may be the same or different. An end of a first segment is then connected to an end of a second segment to form a ring-shaped drug delivery device. The first and second drug-permeable polymeric substances may be a thermoplastic polymer, such as an ethylene-vinyl acetate copolymer. The foregoing method may be repeated with a third drug-permeable polymeric substance and a third drug to form a third unitary segment. Additional segments may be prepared by the same method. The connection of the segments may be performed using an adhesive material or by annealing the ends of the segments with the same or a different thermoplastic polymer. In an alternate embodiment, the ring-shaped drug delivery device is formed by preparing individual segments, instead of rings, and connecting the ends of the segments to form the ring-shaped drug delivery device.

In another aspect the invention relates a method of making a ring-shaped drug delivery device. The method comprises mixing a first drug-permeable polymeric substance with a first drug to form a first polymeric mixture, injecting the first polymeric mixture into a mold to form a first unitary segment. The method is then repeated with a second drug-permeable polymeric substance and a second drug to form a second unitary segment and thus forming the drug delivery device. The first and second drug-permeable polymeric substances may be the same or different. The first and second drug-permeable polymeric substances may be a thermoplastic polymer, such as an ethylene-vinyl acetate copolymer. The foregoing method may be repeated with a third drug-permeable polymeric substance and a third drug to form a third unitary segment. Additional segments may be prepared by the same method.

In another aspect, the present invention relates to a method for the treatment of a benign ovarian secretory disorder in a female mammal, such as polycystic ovarian disease (PCOD). The method comprises providing a drug delivery device comprising at least two segments, wherein the first segment comprises a drug-permeable polymeric substance and a luteinizing hormone releasing hormone (LHRH) or one of its agonistic or antagonistic analogues or a small molecular weight mimic that either binds to the GnRH receptor or blocks its subsequent mechanism of action, and wherein the second segment comprises the drug-permeable polymeric substance and an estrogenic steroid. The drug delivery device is then inserted into the vagina of the female mammal to release a therapeutically effective amount of the LHRH and an effective amount of the estrogenic steroid or estrogen receptor modulator (to avoid the metabolic consequences of the castrational state induced by the LHRH). The drug delivery device may further comprise a third segment, which comprises the drug-permeable polymeric substance and a progestational steroid or a progestin receptor modulator, and which releases an effective amount of the progestational steroid. The drug-permeable polymeric substance may be a thermoplastic polymer, such as an ethylene-vinyl acetate copolymer. The drug delivery device may be in the shape of a ring, a wafer, or a suppository, preferably a ring shape. The benign ovarian secretory disorder may be polycystic ovarian disease. The benign ovarian secretory disorder may be characterized by excessive ovarian androgen secretion, excessive ovarian estrogen secretion, hyperthecosis, hirsutism, dysfunctional uterine bleeding, amenorrhea, or anestrus. The female mammal may be a human female. The estrogen steroid may be estradiol, estradiol benzoate, estradiol cypionate, estradiol dipropionate, estradiol enanthate, conjugated equine estrogen, estriol, estrone, estrone sulfate, ethinyl estradiol, estrofurate, quinestrol or mestranol. The estrogen steroid may also be a selective estrogen receptor modulators such as tamoxifen, raloxifene, clomiphene, droloxifene, idoxifene, toremifene, tibolone, ICI 182,780, ICI 164,384, diethylstilbesterol, genistein, nafoxidine, moxestrol, 19-nor-progesterone derivatives, or 19-nor-testosterone derivatives. The progestation steroid may be progesterone, 17-hydroxy progesterone derivatives, 19-nor-testosterone derivatives, 19-nor-progesterone derivatives norethindrone, norethindrone acetate, norethynodrel, norgestrel, norgestimate, ethynodiol diacetate, allylestrenol, lynoestrenol, fuingestanol acetate, medrogestone, norgestrienone, dimethiderome, ethisterone, cyproterone levo-norgestrel, dl-norgestrel, cyproterone acetate, gestodene, desogestrol, dydrogesterone, ethynodiol diacetate, medroxyprogesterone acetate, megestrol acetate, phytoprogestins, or an animal-derived progestin or metabolic derivatives thereof. The progestational steroid may also be a selective progestin receptor modulator such as RU486, CDB2914, a 19-nor-progesterone derivative, a 19-nor-testosterone derivative, a 6-aryl-1,2-dihydro-2,2,4-trimethylquinoline derivative, a 5-aryl-1,2-dihydro-5H-chromeno[3,4-f]quinoline derivative, a 5-alkyl 1,2-dihydrochomeno[3,4-f]quinoline derivative, or a 6-thiophenehydroquinoline derivative.

In another aspect, the invention relates to preventing pregnancy in a female mammal. The method comprises providing a drug delivery device comprising: (1) a first segment comprising a drug-permeable polymeric substance and a luteinizing hormone releasing hormone (LHRH) or one of its agonistic or antagonistic analogues or a small molecular weight mimic that either binds to the GnRH receptor or blocks its subsequent mechanism of action, (2) a second segment comprising the drug-permeable polymeric substance and an estrogenic steroid or selective estrogen receptor modulator (SERM), and (3) a third segment comprising the drug-permeable polymeric substance and a progestational steroid or selective progestin receptor modulator (SPRM). The drug delivery device is then inserted into the vagina of the mammal to release a therapeutically effective amount of the LHRH, an effective amount of the estrogenic steroid or selective estrogen receptor modulator (SERM), and an effective amount of the progestational steroid or SPRM to the female mammal. The drug-permeable polymeric substance may be a thermoplastic polymer, such as an ethylene-vinyl acetate copolymer.

The drug delivery device may be in the shape of a ring, a wafer, or a suppository, preferably a ring shape.

In yet another aspect, the invention relates to a method of treating a decrease in estrogen secretion in a woman exhibiting symptoms of a cessation of cyclical ovulation and/or the peri-menopause. In one embodiment, the method comprises providing a drug delivery device comprising: (1) a first segment comprising a drug-permeable polymeric substance and a luteinizing hormone releasing hormone (LHRH) or one of its agonistic or antagonistic analogues or a small molecular weight mimic that either binds to the GnRH receptor or blocks its subsequent mechanism of action, (2) a second segment comprising the drug-permeable polymeric substance and a hormone replacement steroid, such as an estrogenic steroid or selective estrogen receptor modulator (SERM), and (3) a third segment comprising the drug-permeable polymeric substance and a progestational steroid or selective progestin receptor modulator (SPRM). In an optional embodiment, the drug delivery device further comprises a fourth segment, which comprises a drug-permeable polymeric substance and an androgen or a selective androgen receptor modulator (SARM). The drug delivery device is then inserted into the vagina of the woman to release effective amounts of the LHRH, sex steroids and/or sex steroid modulators. The estrogen component of the hormone replacement steroid may be an estrogenic steroid, such as a naturally occurring estrogen or a synthetic estrogen. The estrogenic steroid may be estradiol, estradiol benzoate, estradiol cypionate, estradiol dipropionate, estradiol enanthate, conjugated equine estrogen, estriol, estrone, estrone sulfate, ethinyl estradiol, estrofurate, quinestrol or mestranol or other estrogenic steroids.

In still another aspect, the invention relates to a method of treating a decrease in estrogen secretion in a woman exhibiting symptoms of a cessation of cyclical ovulation and/or the menopause. The method comprises providing a drug delivery device comprising at least two segments, wherein the first segment comprises a drug-permeable polymeric substance and a hormone replacement steroid, such as an estrogenic steroid or selective estrogen receptor modulator (SERM), and wherein the second segment comprises a drug-permeable polymeric substance and a progestational steroid or a selective progestin receptor modulator (SPRM). In an optional embodiment, the drug delivery device further comprises a third segment, which comprises a drug-permeable polymeric substance and an androgen or a selective androgen receptor modulator (SARM). The drug delivery device is then inserted into the vagina of the woman to release an effective amount of the hormone replacement steroid. The estrogen component of the hormone replacement steroid may be an estrogenic steroid, such as a naturally occurring estrogen or a synthetic estrogen, such as those described above.

In still a further aspect, the invention relates to a method for relieving the symptoms and signs associated with menopausal, perimenopausal and post-menopausal periods in a woman having these periods and in need of estrogen therapy. The method comprises providing a drug delivery device having a first segment and a second segment, wherein the first segment comprises a drug-permeable polymeric substance and an estrogenic steroid. The drug delivery device is then inserted into the vagina of the woman to release an effective amount of the estrogenic steroid. The drug-permeable polymeric substance may be a thermoplastic polymer, such as an ethylene-vinyl acetate copolymer.

DETAILED DESCRIPTION

Figure 1:
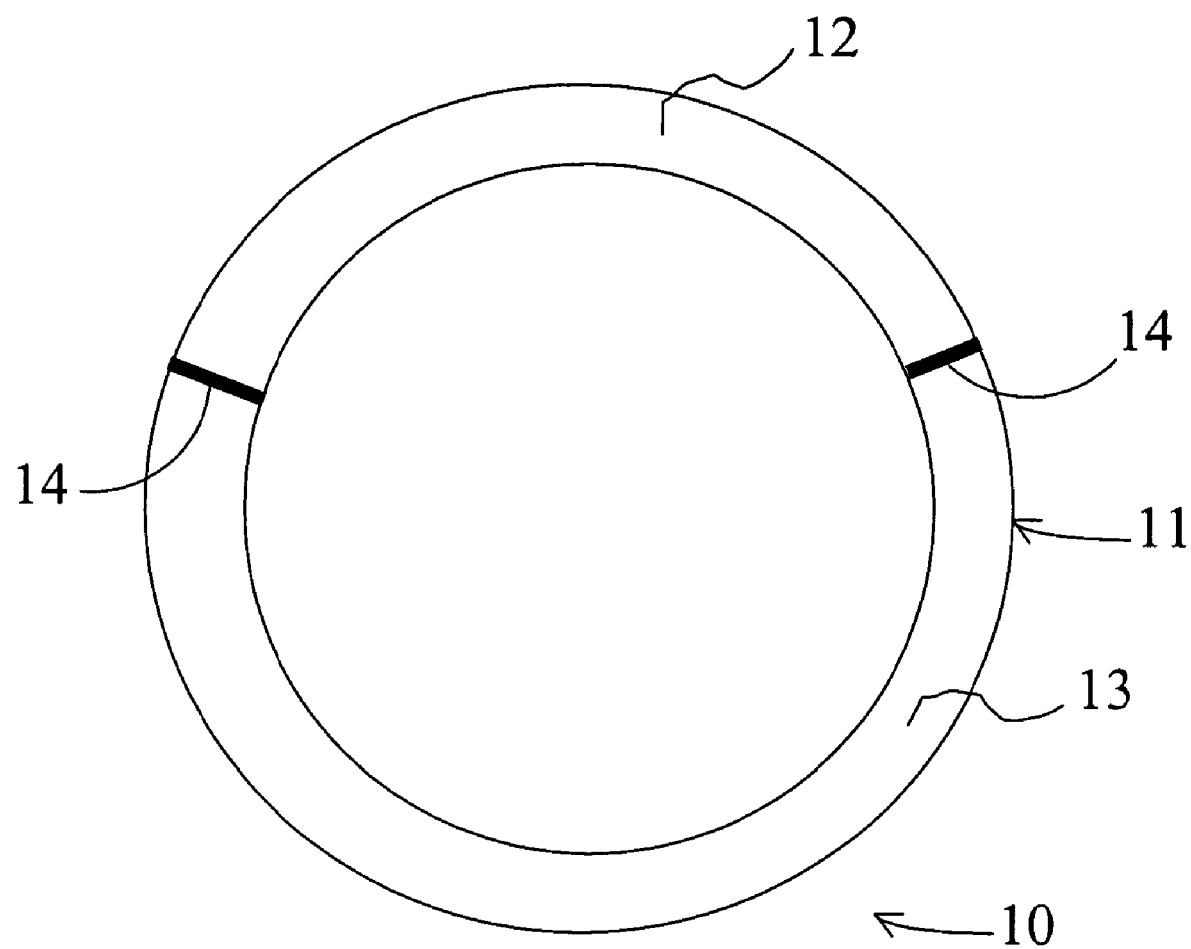
FIG. 1 shows a ring-shaped intravaginal drug delivery device consisting of two segments 12 and 13, which are connected to each other by a coupling means.

The present invention relates to a drug delivery device, a method for delivering a drug to a female mammal, a method of making a ring-shaped drug delivery device, methods for the treatment of a benign ovarian secretory disorder, methods of contraception and methods for hormone replacement therapy.

The drug delivery device, which comprises a drug-permeable polymeric substance, has at least two unitary segments. The segments are preferably joined end to end to form a ring shape. At least one of the segments comprises a mixture of the drug-permeable polymeric substance and a drug, wherein the drug is substantially uniformly dispersed throughout the segment. The invention further relates to a drug delivery system for the simultaneous release of a plurality of drugs, wherein the system releases the drugs in a substantially constant ratio over a prolonged period of time. The method of delivering the drug or combination of drugs to the female mammal comprises the steps of preparing a drug delivery device having two or more unitary segments, positioning the device in the vaginal tract of the female mammal, and maintaining the device in the vaginal tract for a period of time sufficient to deliver a pharmaceutically effective amount of the drug(s) to the female mammal.

As stated above, the drug delivery device, which comprises a drug-permeable polymeric substance, has at least two unitary segments. The device may be in any physiologically acceptable shape, such as a ring, a wafer, or a suppository. In one embodiment, the segments are joined end to end to form a ring shape. At least one of the segments comprises a mixture of the drug-permeable polymeric substance and a drug, wherein the drug is substantially uniformly dispersed throughout the segment. Because of its unique design, the drug delivery device of the present invention provides simultaneous release of a plurality of drugs, in a substantially constant ratio over a prolonged period of time.

The drug delivery device can be easily manufactured, and provides for the reliable and predictable release of the drug or drug combination. In contrast to known intravaginal drug delivery devices comprising a drug-containing fluid core or reservoir, the solid thermoplastic devices used in the methods of the present invention are not susceptible to rupture and the consequent leakage of drug-containing fluid. Moreover, unlike existing devices comprising multiple layers or compartments, the devices described herein can be easily and cheaply manufactured using conventional extrusion technology.

The thermoplastic polymer used in the manufacture of the device may be any thermoplastic polymer or elastomer material suitable for pharmaceutical use, such as polysiloxanes, polyurethane, polyethylene, ethylene-vinyl acetate copolymers, cellulose, copolymers of polystyrene, polyacrylates and various types of polyamides and polyesters. The ethylene-vinyl acetate copolymer (EVA) is highly preferred due to its excellent mechanical and physical properties (e.g., solubility of the drug in the material). The EVA material can be any commercially available ethylene-vinyl acetate copolymer, such as the products available under the names Elvax®, Evatane®, Lupolen®, Movriton®, Ultrathene® and Vestypar®.

The intravaginal drug delivery device used in the methods of the present invention can be manufactured in any size as required. In the case of human use, the ring-shaped device has an outer diameter from about 40 mm to about 80 mm, and preferably between 50 mm and 60 mm; the cross-sectional diameter is preferably between about 1 mm and about 12 mm, and preferably between 2 and 6 mm.

The present invention also relates to methods for the treatment of a benign ovarian secretory disorder and for preventing pregnancy in a female mammal, as well as methods for treating a decrease in estrogen secretion in a woman exhibiting symptoms of a cessation of cyclical ovulation and for relieving the symptoms and signs associated with menopausal, perimenopausal and post-menopausal periods in a woman. The methods comprise providing a drug delivery device having two or more unitary segments, wherein at least one of the segments comprises a drug-permeable polymeric substance and a drug. The choice of drug(s) will depend on the particular application or indication being treated. For example, for contraceptive uses and the treatment of a benign ovarian secretory disorder, the drugs are a luteinizing hormone releasing hormone (LHRH) and an estrogenic steroid and sequential progesterone/progestine; for contraceptive purposes, the drugs are LHRH, an estrogenic steroid, and progestational steroid; and, for treating a decrease in estrogen secretion, the drug is a hormone replacement steroid, such as an estrogenic steroid. An estrogenic steroid is also the drug used in methods for relieving the symptoms and signs associated with menopause. Similarly, progesterone can be used in methods for relieving the symptoms and signs associated with menopause. The drug delivery device is then inserted into the vagina of the female mammal, such as a human female, to release an effective amount(s) of the drug(s). The drug-permeable polymeric substance may be a thermoplastic polymer, such as an ethylene-vinyl acetate copolymer. The drug delivery device may be in the shape of a ring, a wafer, or a suppository, preferably a ring shape.

The following detailed description discloses how to practice the methods of the present invention. It also describes how to make and use the intravaginal drug delivery device to deliver a pharmaceutically effective amount of a drug to a female mammal.

I. Definitions

For convenience, the meaning of certain terms and phrases used in the specification, examples, and appended claims are provided below.

As used herein, the terms "unitary segment" or "segment" refer to a solid material having a substantially uniform or homogenous composition throughout. The terms "segment" and "unitary segment" specifically exclude vaginal rings or portions thereof comprising a core or reservoir and an inner and/or outer layer of material, such as a skin, wall, membrane, coating, or polymeric layer or layers.

As used herein, the terms "unitary cylindrical segment" and "unitary cylindrical rod" refer to a solid cylinder or rod-shaped material having a substantially uniform or homogenous composition throughout. The terms "segment" and "unitary cylindrical rod" specifically exclude vaginal rings or portions thereof comprising a core or reservoir and an inner and/or outer layer of material, such as a skin, wall, membrane, coating, or polymeric layer or layers.

As used herein, the term "drug-permeable" refers to a polymeric material through which a drug can diffuse and thus be absorbed for local and/or systemic effects in a mammal. The term "non-absorbable" means there is no absorption of the polymeric material in the vaginal tract of the female mammal being treated. The term "non-erodible" means that the polymeric material does not erode in the vaginal tract of the female mammal. The term "non-degradable" means that the polymeric material does not degrade or break down in vivo. The term "compatible" means compatible both with the environment of the vaginal tract in that there is no breakdown of the tensile nature or structural integrity of the device due to the contents of the vagina. Likewise there is no deleterious action on the sensitive tissue in the area of placement in the vaginal tract. Widely varying types of polymeric material are suitable in providing these non-toxic, drug-permeable properties, for example polysiloxanes, polyurethane, polyethylene, ethylene-vinyl acetate copolymers, cellulose, copolymers of polystyrene, polyacrylates and various types of polyamides and polyesters. The above-mentioned polymers can be used in a porous or microporous form. The term "thermoplastic polymer" refers to a polymeric material which is capable of being softened by heating and hardened by cooling through a temperature range characteristic of the polymer, and in the softened state can be shaped by flow into devices by molding or extrusion.

As used herein, the term "coupling means" refers to a method, mechanism, material or device for joining or connecting the ends of two unitary segments or unitary cylindrical rods to each other. The term "adhesive material," as used herein refers to an inert bonding agent, glue, or other substance having sufficient adhesive properties to bind the ends of the segments. The adhesive material can be, for example, a medical grade silicone adhesive.

As used herein, the terms "patient" and "female mammal" are used interchangeably to refer to a human or other animal in which it is desired to provide a medical treatment or contraceptive agent.

By "simulating or inducing the follicular or luteal phase of the menstrual cycle" is meant to simulate or induce the sex steroid hormone milieu in the patient so as to provide such patient with levels of sex steroid hormones that approximate the endocrine environment of a normal follicular or luteal phase.

As used herein, "benign ovarian secretory disorders" refers to any of a variety of benign conditions in which suppression of ovarian function is important. These conditions largely center around benign secretory disorders of the ovaries such as (a) polycystic ovarian disease and hyperandrogenic hirsutism, and/or (b) excessive ovarian sex steroid secretion of androgens, estrogens or progestins. Benign ovarian secretory disorders may be characterized, for example, by hyperthecosis, hirsutism, dysfunctional uterine bleeding, amenorrhea, anestrus, or oligomenorrhea.

By "excessive" ovarian sex steroid secretion of androgens, estrogens or progestins is meant secretion of androgens, estrogens or progestins in amounts such that the ratios of the androgens, estrogens or progestins in the serum of a patient are abnormal when compared to normal levels of such androgens, estrogens or progestins for the female mammal. Therefore, "excessive" estrogen secretion is meant to encompass conditions wherein the ovaries secrete estrogen levels that do not conform to the normal levels encountered in female reproduction physiology such as the normal menstrual cycle; "excessive" progestin secretion is meant to encompass conditions wherein the ovaries secrete too much progestin, e.g., levels excessive or inappropriate for normal physiologic levels in normal women; and, "excessive" androgen secretion is meant to encompass conditions wherein the ovaries secrete too much androgen, e.g., levels above those encountered in normal female physiology.

As used herein, "LHRH" and "LHRH composition" refer to luteinizing hormone releasing hormone (LHRH), LHRH analogues, LHRH agonists and LHRH antagonists analogues (peptide and/or non-peptide in nature), and/or any compound (peptide or non-peptide) that can bind to the LHRH receptor and/or can produce hypogonadotropic hypogonadism in a mammal, such as a human. The LHRH that may be used in this invention are physiologically active peptides or non-peptide analogues capable of binding to the LHRH receptor and are gonadotropin secretory inhibitors or gonadotropin-receptor-effect blockers. LHRH is characterized as a decapeptide having the following structure:

SEQ ID NO:1 p-Glu-His-Trp-Ser-Tyr-Gly-Leu-Arg-Pro-Gly-NH$_2$

As used herein, the terms "LHRH agonist" and "LHRH antagonist" refer to such physiologically active peptides or non-peptide analogues which respectively enhance or inhibit the biological activity of LHRH. For example, LHRH agonists useful in the methods of the invention include, but are not limited to, Cystorelin (Hoechst), Gonadorelin (Ayerst), Zoladex™ (ICI), Buserelin (Boechst), Leuprolide (Abbott/Takeda), Decapeptyl (Debiopharm, Ipsen/Beaufour), Nafarelin (Syntex), Lutrelin (Wyeth) and Histrelin (Ortho). LHRH, LHRH analogues, LHRH agonists and LHRH antagonists are well known in the art and are described in numerous patents, including the following patents: U.S. Pat. Nos. 4,705,778, 4,690,916, 4,530,920; 4,481,190; 4,419,347; 4,341,767; 4,318,905; 4,234,571; 4,386,074; 4,244,946; 4,218,439; 4,215,038; 4,072,668; 4,431,635; 4,317,815; 4,010,125; 4,504,414; 4,493,934; 4,377,515; 4,504,414; 4,338,305; 4,089,946; 4,111,923; 4,512,923; 4,008,209; and 4,010,149, all incorporated herein by reference. The LHRH compositions described in the above patents may be used in the methods of this invention.

As used herein, the terms "estrogenic steroid" and "estrogen" are used interchangeably to refer to an agent, natural or synthetic, that exerts biological effects characteristic of estrogenic hormones such as estradiol. As used herein, the terms "estrogenic steroid" and "estrogen" also encompasses "conjugated estrogens," which are an amorphous preparation of naturally occurring, water-soluble, conjugated forms of mixed estrogens that typically are obtained from the urine of pregnant mares (e.g., sodium estrone sulfate). Also included are "esterified estrogens," which are a mixture of the sodium salts of sulfate esters or glucanoride of sulfate conjugates of estrogenic substances. Examples of suitable estrogens include, without limitation, estradiol valerate, estradiol benzoate, 17-β estradiol, estradiol cypionate, estrone, piperazine estrone sulfate, estriol, ethyl estradiol, polyestradiol phosphate, estrone potassium sulfate, benzestrol, chlorotrianisene, methallenestril, dienestrol, diethylstilbestrol diphosphate, mestranol, diethylstilbestrol (DES), quinestranol, phytoestrogens, animal-derived estrogens (e.g., equine estrogens), and metabolic derivatives of animal-derived estrogens. These also include any steroid or non-steroidal compound that binds either to the known estrogen receptors that exist within cells or to estrogen receptors that bind to extracellular membranes and cause biologic effects that mimic those of estradiol or other estrogenic compounds.

As used herein, the terms "progestational steroid" and "progestin" are used interchangeably to refer to an agent, natural or synthetic, that effects some or all of the biological changes produced by progesterone, which is a hormone of the corpus luteum. For example, a progestin can induce secretory changes in the endometrium. Examples of progestins include, without limitation, progesterone, 17-hydroxy progesterone derivatives, 19-nor-testosterone derivatives, 19-nor-progesterone derivatives norethindrone, norethindrone acetate, norethynodrel, norgestrel, norgestimate, ethynodiol diacetate, allylestrenol, lynoestrenol, fuingestanol acetate, medrogestone, norgestrienone, dimethiderome, ethisterone, cyproterone levo-norgestrel, dl-norgestrel, cyproterone acetate, gestodene, desogestrol, dydrogesterone, ethynodiol diacetate, medroxyprogesterone acetate, megestrol acetate, phytoprogestins, animal-derived progestins, and metabolic derivatives of animal-derived progestins. These compounds also include any steroidal or non-steroidal compounds that bind to the cytoplasmic or membrane bound progesterone and mimic any of the biologic effects of progesterone or progestins.

As used herein, the terms "androgenic steroid" and "androgen" are used interchangeably to refer to a natural or synthetic agent that stimulates activity of the accessory male sex organs and/or muscle development and/or encourages development of male sex characteristics. Examples of suitable androgens include, without limitation, testosterone, methyltestosterone, fluoxymesterone, testosterone cypionate, testosterone enanthate, testosterone propionate, oxymetholone, ethylestrenol, oxandrolone, nandrolone phenpropionate, nandrolone decanoate, testosterone buccilate, stanozolol, dromostanolone propionate, androstenedione, dehydropepiandrosterone, dehydroepiandrosterone sulfate (DHEAS), dihydrotestosterone, phytoandrogens, animal-derived androgens, and metabolic derivatives of animal-derived androgens. This also included any steroidal or non-steroidal compounds that bind to either the cytoplasmic or membrane bound androgen receptor and produce biologic effects that mimic testosterone or other androgenic compounds.

A "selective estrogen receptor modulator" ("SERM") is a compound that is an estrogen analog and which exerts tissue-selective effects. Such compounds can function as estrogen antagonists or partial agonists. Examples of suitable SERMs include tamoxifen, raloxifene, clomiphene, droloxifene, idoxifene, toremifene, tibolone, ICI 182,780, ICI 164,384, diethylstilbesterol, genistein, nafoxidine, moxestrol, 19-nor-progesterone derivatives, and 19-nor-testosterone derivatives.

A "selective androgen receptor modulator" ("SARM") is a compound that is an androgen analog and which exerts tissue-selective effects. Such compounds can function as androgen antagonists or partial agonists. Examples of suitable SARMs include cyproterone acetate, hydroxyflutamide, bicalutamide, spironolactone, 4-(trifluoromethyl)-2(1H)-pyrrolidino[3,2-g]quinolinone derivatives, 1,2-dihydropyridono[5,6-g]quinoline derivatives, and piperidino[3,2-g]quinolinone derivatives.

A "selective progestin receptor modulator" ("SPRM") is a compound that is an progesterone analog and which exerts tissue-selective effects. Such compounds can function as progesterone antagonists or partial agonists. Examples of suitable SPRMs include RU486, CDB2914, 19-nor-progesterone derivatives, 19-nor-testosterone derivatives, 6-aryl-1,2-dihydro-2,2,4-trimethylquinoline derivatives, 5-aryl-1,2-dihydro-5H-chromeno[3,4-f]quinoline derivatives, 5-alkyl 1,2-dihydrochomeno[3,4-f]quinoline derivatives, and 6-thiophenehydroquinoline derivatives.

Unless indicated otherwise, the hormonal steroids used in the methods of the present invention (e.g., estrogenic steroids, progestational steroids, and androgenic steroids) include the respective sex steroids (both natural and synthetic, including derivatives and analogues thereof), as well as their respective hormone receptor modulator compounds (e.g., SERMs, SPRMs, and SARMs). Hormonal steroids are well known in the art and are described, for example, in Remington's Pharmaceutical Sciences (16th edition, 1980) at pages 925-939.

A "postmenopausal" woman is one who in the absence of hormone replacement therapy or other medication would experience at least 12 months of amenorrhea or levels of serum follicle-stimulating hormone greater than 30 mIU/ml.

A "perimenopausal" woman is one who in the absence of hormone replacement therapy or other medication would experience a change in her intermenstrual cycle interval and have associated symptoms of estrogen deficiency, such as vasomotor flushes, vaginal dryness, and worsening premenstrual syndrome. Also included are women who in the absence of hormone replacement therapy or other medication would experience less than 12 months of amenorrhea.

As used herein, the term "drug" means any physiologically or pharmacologically active substance that produces a local and/or systemic effect in a mammal, such as a human.

As used herein, "pharmacologically effective amount," "therapeutically effective amount" or simply "effective amount" refers to that amount of a drug effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease or disorder is the amount necessary to effect at least a 25% reduction in that parameter.

II. Drug Delivery Device

By way of example, FIG. 1 shows one embodiment of the present invention. The drug delivery device shown in this figure is offered for illustration only, and is not to be construed as limiting the invention. As one of skill in the art will appreciate, the drug delivery device can be manufactured in a variety of shapes, sizes, and dimensions, depending upon the particular mammal to be treated, as well as the nature and severity of the condition to be treated. In FIG. 1, drug delivery device 10 comprises a body 11 sized, shaped and adapted for placement in the vaginal tract of a human. The drug delivery device 10 comprises a body 11 formed of a polymer that releases a drug(s) by diffusion into the vaginal tract of the patient. The drug delivery device 10 shown in FIG. 1 comprises two unitary cylindrical segments 12 and 13, which are connected to each other by a coupling means 14. Although FIG. 1 depicts unitary cylindrical segments one of skill in the art will appreciate the segments can be manufactured in a variety of shapes, sizes, and dimensions. The two segments can also be directly fused without the need for a coupling means. Such a formulation is contemplated by the multiple port mold of Example 9. Although the illustrated device comprises two segments, the drug delivery device of the present invention can comprise three, four, five, six, or more segments. The number and size of the segments used for a particular application will depend, inter alia, on the number of drugs to be delivered the dosages of the drugs, and the need for a placebo segment(s) to prevent diffusion and interaction of the drugs within the device.

The drug delivery device of the present invention is formed of a drug-permeable polymeric material. Suitable polymers include, for example, olefin and vinyl-type polymers, carbohydrate-type polymers, condensation-type polymers, rubber-type polymers, and organosilicon polymers. In a presently preferred embodiment, the polymer is a non-absorbable thermoplastic polymer. Polymers that can be used for manufacturing the drug delivery device include, without limitation, poly(ethylene-vinyl acetate), poly(methylacrylate), poly(butylmethacrylate), plasticized poly(vinylchloride), plasticized nylon, plasticized soft nylon, plasticized poly(ethylene terephthalate), poly(ethylene), poly(acrylonitrile), poly(trifluorochloroethylene), poly(4,4'-isopropylene-diphenylene carbonate), poly(ethylenevinyl esters), poly(vinyl chloridediethyl fumarate), poly(esters of acrylic and methacrylic), cellulose acetate, cellulose acylates, partially hydrolyzed poly(vinyl acetate), poly(vinyl butyral), poly(amides), poly(vinyl carbonate), poly(urethane), poly(olefins), and the like. These polymers and their physical properties are known to the art and can be synthesized according to the procedures disclosed, for example, in Encyclopedia of Polymer Science and Technology (Interscience Publishers, Inc., New York, 1971) Vol. 15, pp. 508-530; Polymers (1976), Vol. 17, 938-956; Technical Bulletin SCR-159, 1965, Shell Corp., New York; and references cited therein; and in Handbook of Common Polymers, Scott and Roff (CRC Press, Cleveland, OH, 1971).

In a preferred embodiment, the thermoplastic polymer is an ethylene-vinyl acetate (EVA) copolymer. EVA copolymers, which are well known and commercially available materials, are particularly useful for the controlled release of drugs by diffusion. Very suitable EVA polymers include, for example, the EVA material manufactured by Aldrich Chemical Co. (Cat. No. 34,050-2); Evatane® with the designations 28-150, 28-399, and 28-400, supplied by ICI and 28.420, and in particular 28.25 and 33.25 supplied by Atochem; and Elvax® with the designations 310, 250, 230, 220, and 210, supplied by Du Pont de Nemours.

The release of the drug by a drug delivery device comprising EVA is determined to a large extent by the vinyl acetate content of the material. In its broadest aspects, the present invention contemplates use of EVA copolymers having a vinyl acetate content of about 4 to 80% by weight of the total, and a melt index of about 0.1 to 1000 grams per ten minutes. Melt index is the number of grams of polymer which can be forced through a standard cylindrical orifice under a standard pressure at a standard temperature, and thus is inversely related to the molecular weight of the polymer. Preferably, the EVA has a vinyl acetate content of about 4 to 50% by weight and a melt index of about 0.5 to 250 grams per ten minutes. In general, the rate of passage of a drug through the polymer is dependent on the molecular weight and solubility of the drug therein, as well as on the vinyl acetate content of the polymer. This means that selection of particular EVA compositions will depend on the particular drug to be delivered. By varying the composition and properties of the EVA, the dosage rate per area of the device can be controlled. Thus, devices of the same surface area can provide different dosage of a drug by varying the characteristics of the EVA copolymer. The release of the drug by a drug delivery device comprising EVA is also controlled by the surface area of the segment. For example, in order to increase the rate of release of the drug one could increase the length and/or circumference of the segment.

In addition to varying the percentage of vinyl acetate in the copolymer and the melt index or molecular weight, the properties of the copolymer can be changed by selectively hydrolyzing its acetate groups to alcohol groups. By converting a portion of the vinyl acetate units of the polymer to vinyl alcohol units, the polymer is rendered more hydrophilic and the rate of passage of relatively hydrophilic drugs is increased. The percentage of vinyl acetate units hydrolyzed to vinyl alcohol units can vary widely but typically from about 20 to 60% are converted. This partial hydrolysis is a well known procedure and can be accomplished under standard conditions well known in the art. Exemplary hydrolysis procedures are described in U.S. Pat. Nos. 3,386,978 and 3,494,908, both of which are incorporated by reference herein.

The rate of diffusion of a drug from the drug delivery device is broadly determined by measuring the rate of the drug transferred from one chamber through a sintered glass filter of known pore size and thickness into another chamber and calculating from the obtained data the drug transfer rate. The procedure is well known in the art, and described, for example, in Proc. Roy. Sci. London, Ser. A, 148:1935; J. Pharm. Sci. (1966) 55:1224-1229; and references cited therein. The diffusion coefficient of a drug can also be experimentally determined by using the same or similar apparatus. Methods for determining the diffusion coefficient are described in Diffusion in Solids, Liquids and Gases, by W. Jost (Rev. Ed., Academic Press Inc. NY; 1960), Chapter XI, pp. 436-488. Preferably, the drug(s) to be delivered has a molecular weight of between 50 and 2000, more preferably between 200 and 1300.

The solubility of a drug in an EVA copolymer is determined by preparing a saturated solution of the drug and ascertaining, by analysis, the amount present in a defined area of the copolymer material. For example, the solubility of the drug in the EVA copolymer is determined by first equilibrating the polymer material with a saturated solution of the drug at a known temperature, for example 37° C., or with a pure liquid drug, if the drug is a liquid at 37° C. Next, the drug is desorbed from the saturated polymer material with a suitable solvent for the drug. The resultant solution is then analyzed by standard techniques such as ultraviolet, visible spectrophotometry, refractive index, polarography, electrical conductivity and the like, to calculate the concentration or solubility of the drug in the material.

The solubility of a drug in a polymeric material can be determined by various art known techniques. Typical methods used for the measurement of solubility are chemical analysis, measurement of density, refractive index, electrical conductivity, and the like. Details of various methods for determining solubilities are described in U.S. Public Health Service Bulletin No. 67 of the Hygienic Laboratory; Encyclopedia of Science and Technology (McGraw-Hill, Inc.; 1971) 12:542-556; and Encyclopaedic Dictionary of Physics (Pergamon Press, Inc; 1962) 6:545-557. Also, according to Fick's Law, the rate of drug solution is directly proportional to the area (A) of the drug, A in $cm^2$, as exposed to polymeric material and inversely proportional to the length of the path through which the dissolved drug must diffuse (see Remington Pharmaceutical Science (Mack Publishing Company, 14th Ed., 1970), pp. 246-269.

In a preferred embodiment, the drug delivery device of the invention provides "zero order kinetic" drug administration, in which a drug is released in a steady state, thus providing a corresponding predictable absorption and metabolism of the drug in the body tissues. In this manner, the delivery of drugs may be "targeted" to the specific body organ, where the intended therapeutic effect is desired; other organs such as liver, in which unintended effects may occur, may be bypassed. Thus, the efficient metabolic and therapeutic use of a drug or drug combination may be enhanced, and the development of adverse metabolic side effects may be reduced. "Zero order kinetic" drug administration is well known in the art. Other methods for the controlled timed release of predetermined amounts of pharmacologically active compositions at a target site are also known. Methods for achieving targeted delivery of drugs include, for example, the use of micellar structures, such as liposomes, capsids, capsoids, polymeric nanocapsules, and polymeric microcapsules. Liposomal suspensions (including liposomes targeted to cells with monoclonal antibodies to specific viral antigens) are particularly useful for practicing the methods of the present invention. Liposomal formulations can be prepared according to methods known to those skilled in the art, for example, as described in U.S. Pat. No. 4,522,811; PCT publication WO 91/06309; and European patent publication EP-A-43075, which are incorporated by reference herein. The use of highly hydrophobic formulations, such as liposomes, also increases the absorption rate of the drug through the vaginal epithelium.

In another embodiment, the polymeric matrix is capable of being degraded by ultrasonic energy such that the incorporated drug is released at a rate within a desired release range, or, in the case of nondegradable polymers, release is enhanced presumably due to the effects of cavitation or other mechanical effects. Representative suitable polymers for this embodiment include polyanhydrides having the formula described in U.S. Pat. No. 4,657,543 (Langer et al.), which is incorporated by reference in its entirety herein. The monomers in the copolymer can be distributed regularly or at random. Since the anhydride linkage is highly reactive toward hydrolysis, it is preferable that the polymer backbone be hydrophobic in order to attain the heterogeneous erosion of the encapsulated composition. Hydrophobicity can be regulated easily, for example, by regulating the concentration of aromatic moieties in the linking backbone, or by monitoring the monomer ratio in the copolymer. A particularly suitable backbone comprises the acid such as 1-phenylamine, tryptophan, tyrosine or glycine. Other suitable polymers include ethylene-vinyl acetate, polylactic acid, polyglutamic acid, polycaprolactone, lactic/glycolic acid copolymers, polyorthoesters, polyamides or the like. Non-degradable polymers include ethylene-vinyl acetate, silicone, hydrogels such as polyhydroxyethylmethacrylate, polyvinyl alcohol, and the like.

In addition to providing excellent release properties, the preferred compatible, non-absorbable, non-toxic polymeric materials used in the manufacture of the inventive drug delivery device (e.g., EVA copolymer, organopolysiloxane, or other rubbery-type resilient material) do not induce a significant tissue reaction at the site of placement in the vaginal tract of the female mammal. As a result, the drug delivery device of the present invention is useful in a wide variety of applications, such as those described in sections III-VI.

The dosage unit amount for conventional beneficial drugs as described herein is well known in the art (see, e.g., *Remington's Pharmaceutical Science* (Fourteenth ed., Part IV, Mack Publishing Co., Easton, Pa., 1970)). The amount of drug incorporated in the drug delivery device varies depending on the particular drug, the desired therapeutic effect, and the time span for which the device provides therapy. Since the inventive device is intended to provide dosage regimes for therapy for a variety of applications and indications, there is no critical upper limit on the amount of drug incorporated in the device. Similarly, the lower limit will depend on the activity of the drug and the time span of its release from the device. Thus, it is not practical to define a range for the therapeutically effective amount of drug to be incorporated in or released by the device.

The relative amount(s) of the drug(s) to be released can be modified over a wide range depending upon the drug to be administered or the desired effect. Generally, the drug can be present in an amount which will be released over controlled periods of time, according to predetermined desired rates, which rates are dependent upon the initial concentration of the active substance in the polymeric matrix. In the second embodiment described above, the rate will also depend upon the level of ultrasonic energy to which it is subjected. This necessarily implies a quantity of active substance greater than the standard single dosage. Proportions suitable for the purposes of this invention can range from about 0.01 to 50 parts by weight of the active substance to between about 99.99 and about 50 parts by weight of the polymeric matrix, preferably between about 10 and about 30 parts by weight in the case of a drug to be implanted to give 100 parts per weight of the final system. The polymeric matrix in the composition to be released can be admixed in any convenient manner, for example by mixing the components as powders and subsequently forming the mixture into a desired shape such as by thermal forming at a temperature less than that which the composition will become degraded and at which the polymer has desired morphological properties. Such procedures are described in detail in the examples provided herein.

The polymeric mixture utilized in the drug delivery device used in the methods of the present invention can be manufactured by standard techniques provided that such manufacture includes process steps such as blending, mixing or the equivalent thereof for structurally defining the system comprising the drug(s) to be released and the polymeric matrix. For example, one suitable method for making the inventive devices comprises mixing the polymer and an appropriate solvent, thereby to form a casting solution, mixing a known amount of the drug to be released in the casting solution, charging the solution into a mold and then drying the mold, optionally under vacuum, causing the polymer to precipitate in forming the matrix with the drug to be released therein. Alternatively, the polymer in the form of a powder can be admixed with the drug to be released in the form of a powder and then molded under adequate temperature and pressure to the desired shape, through injection, compression, or extrusion. When two or more drugs are to be delivered, the foregoing steps of manufacture are repeated for each individual drug, thus forming a separate molded polymeric mixture for each drug. The individual molded polymeric mixtures, each preferably containing a different drug, are then cut into pieces of the required length using conventional cutting techniques, thus producing a plurality of uniform segments. The drug delivery device or system for simultaneous delivery of multiple drugs is then assembled by joining together, directly or indirectly, at least one segment of the molded polymeric mixture for each drug to be delivered. Preferably, the uniform segments are assembled to form a ring shape, which has a thickness between about 1 mm and about 5 mm. The drug delivery devices of this invention can be manufactured in a wide range of shapes, sizes and forms for delivering the drug(s) to different environments of use.

Alternatively, when two or more drugs are to be delivered, each drug:polymer mix can be molded together under adequate temperature and pressure to the desired shape, through injection, compression, or extrusion such that the two drug mixtures form one solid unit and do not require a coupling means. In one embodiment, the drug mixtures are injected, preferably sequentially, into a mold comprising a single port. In an alternative embodiment, as exemplified in Example 8, herein below, the drug mixtures are injected simultaneously or sequentially into a mold having multiple ports. Multiple port moldings are well known and commercially available in the art. Such molding may be modified or customized for a particular application as will be appreciated by those of skill in the art.

In one embodiment, discussed briefly above, the ends of the segments are joined together to form a drug delivery device using a coupling means. The coupling means can be any method, mechanism, device or material known in the art for bonding materials or structures together. Exemplary coupling means include solvent bonding, adhesive joining, heat fusing, heat bonding, pressure, and the like. When a solvent is used, the ends of the segments are moistened with an organic solvent that causes the surfaces to feel tacky, and when placed in contact the surfaces then bond and adhere in a fluid tight union. The ends of the segments can be adhesively united to form a ring-shaped delivery device by applying an adhesive to at least one end of a segment, and then contacting the adhesive coated end or ends. For the above procedures, the solvents include organic solvents such as methylene chloride, ethylene dichloride, trichlorobenzene, dioxan, isophorone, tetrahydrofuran, aromatic and chlorinated hydrocarbons, mixed solvents such as 50/50 ethylene dichloride/diacetone alcohol; 40/60 alcohol/toluene; 30/70 alcohol/carbon tetrachloride, and the like. Suitable adhesives include natural adhesives and synthetic adhesives, such as animal, nitrocellulosic, polyamide, phenolic, amino, epoxy, isocyanate, acrylic, silicate, organic adhesives of polymers, and the like. Adhesives are well known to the art (see, e.g., The Encyclopedia of Chemistry (Second ed.; G. L. Clark and G. G. Hawley, editors; VanNostrand Reinhold Co., Cincinnati, OH; 1966)), as well as solvents (see, e.g., Encyclopedia of Chemical Technology (Kirk-Othmer, Sec. Ed., Vol. 16, Interscience, Publishers Inc., New York, 1969)).

The lengths of the segments of the drug delivery device or system are chosen to give the required performance. Ratios of the lengths of the segments will depend upon the particular therapeutic application, including the desired ratio and dosages of each drug to be delivered. Ratios of the lengths of the segments are contemplated to be between 30:1 and 1:30, preferably between 15:1 and 1:1. When placebo segments are required to prevent drug diffusion and interactions, the lengths of the placebo segments are long enough to prevent excessive mixing of the drugs. The length of the placebo segment depends on the nature of the polymeric substance and its capacity to prevent permeation of the drugs. Preferably, the placebo segment completely prevents mixing of the drugs, since mixing may disturb the release pattern. However, depending upon the drugs, some minor mixing is generally permitted, provided it does affect the release of the drugs in such a manner that plasma levels of the drugs get outside the required values. Placebo segments may also be used to close or complete the ring-shaped structure.

In an alternate embodiment, the drug delivery device is manufactured by preparing unitary rods, rather then segments, then joining the ends of the rods to form a ring-shaped drug delivery device for the simultaneous release of multiple drugs. In this embodiment, the unitary rods are prepared essentially as described above for the segments, except that the polymeric mixture is molded into the shape of a rod rather than a ring. In the case of vaginal rings, the polymeric substance must be sufficiently pliable when dry to allow the rods to be bent and formed into the final ring-shaped device. Thus, the step of cutting the ring into segments may be avoided, provided that the molded rods meet the specifications (e.g., length, diameter, etc.) to deliver the required dosages of drugs. Alternatively, the polymeric mixture may be molded into over-sized cylindrical rods, which are then cut into shorter rods having the required dimensions. Rods of the proper size are then joined end-to-end, as described above for the segments, to form a ring-shaped drug delivery device.

As previously mentioned, the drug delivery device can be manufactured in any size as required. For human use, however, the outer ring diameter will generally be between 40 mm and 80 mm, preferably between 45 mm and 70 mm, and more preferably between 50 and 60 mm. Similarly, the cross sectional diameter will typically be between 0.5 mm and 12 mm, preferably between 0.5 mm and 10 mm, more preferably between 1 mm and 8 mm, even more preferably between 1 and 6 mm, and most preferably between 1 and 5 mm.

III. Administration

In another aspect, the invention relates to a method for delivering a drug to a female mammal. The method involves preparing a drug delivery device, as described above. The device is then positioned in the vaginal tract of the female mammal to be treated, where it is maintained for a period of time sufficient to deliver an effective amount of the drug to the female mammal. Although the present invention is described in terms of an intravaginal drug delivery device, the invention contemplates making and using a device for administering a drug to a male mammal. In this case, the device is manufactured in a shape and size appropriate for use in a male mammal, for example as a subdermal implant or rectal suppository. The male drug delivery device may comprise any suitable active substance for use in a wide variety of applications and for treating a variety of diseases and medical conditions, such as those described below, and particularly male-specific diseases such as prostate cancer.

Because of its convenience, safety, and excellent release properties, the drug delivery device of the present invention is useful in a wide variety of applications, and can be used to treat numerous conditions and disorders. Examples of applications and therapeutic uses for the device include, without limitation, contraception, hormone replacement therapy, polycystic ovarian disease, addiction, imaging, AIDS/HIV, immunology, alcohol-related disorders, infectious diseases, allergy, leukemia/lymphoma, Alzheimer's disease, lung cancer, anesthesiology, metabolic disorders, anti-infectives, neonatology, anti-inflammatory agents, neurological disorders, arthritis, neuromuscular disorders, asthma, nuclear medicine, atherosclerosis, obesity, eating disorders, bone diseases, orthopedic, breast cancer, colon cancer, prostate cancer, cancer, parasitic diseases, cardiovascular diseases, hypertension, toxemia of pregnancy, seizures perinatal disorders, child health, pregnancy, preventative medicine, congenital defects, decision analysis, psychiatric disorders, degenerative neurologic disorders, pulmonary disorders, dementia, radiology, dermatology, renal disorders, diabetes mellitus, reproduction, diagnostics, Rheumatic diseases, stroke, drug discovery/ screen, surgical, endocrine disorders, transplantation, ENT, vaccines, epidemiology, vascular medicine, eye diseases, wound healing, fetal and maternal medicine, women's health, gastrointestinal disorders, gene therapy, genetic diagnostics, genetics, genitourinary disorders, geriatric medicine, growth and development, hearing, hematologic disorders, hepatobiliary disorders, and hypertension.

Any pharmaceutically active agent used to treat the body, and which is capable of diffusing through the polymer and being absorbed by the lining of the vaginal tract, is useful in the present invention. Preferably, though not necessarily, the drug is one that has already been deemed safe and effective for use by the appropriate governmental agency or body. For example, drugs for human use listed by the FDA under 21 C.F.R. 330.5, 331 through 361; 440-460; drugs for veterinary use listed by the FDA under 21 C.F.R. 500-582, incorporated herein by reference, are all considered acceptable for use in the present novel polymer networks. Examples of suitable active substances (drugs) include, without limitation, interferon, anti-angiogenesis factors, antibodies, antigens, polysaccharides, growth factors, hormones including insulin, glucogen, parathyroid and pituitary hormones, calcitonin, vasopressin, renin, prolactin, thyroid stimulating hormone, corticotrophin, follicle stimulating hormone, luteinizing hormone and chorionic gonadotropins; enzymes including soybean, tyrpsin inhibitor, lysozyme, catalase, tumor angiogenesis factor, cartilage factor, transferases, hydrolases, lysases, isomerases, proteases, ligases and oxidoreductases such as esterases, phosphatases, glysidases, and peptidases; enzyme inhibitors such as leupeptin, antipain, chrymostatin and pepstatin; and drugs such as steroids, anti-cancer drugs or antibiotics. Suitable pharmaceuticals for parenteral administration are well known as is exemplified by the Handbook on Injectable Drugs, 6th edition, by Lawrence A. Trissel, American Society of Hospital Pharmacists, Bethesda, Md., 1990 (hereby incorporated by reference).

Additional examples of drugs which may be delivered by drug delivery devices according to this invention include, without limitation, prochlorperzine edisylate, ferrous sulfate, aminocaproic acid, mecamylamine hydrochloride, procainamide hydrochloride, amphetamine sulfate, methamphetamine hydrochloride, benzamphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperzine maleate, anisindone, diphenadione erythrityl tetranitrate, digoxin, isofluorophate, acetazolamide, methazolamide, bendroflumethiazide, chloropromaide, tolazamide, chlormadinone acetate, phenaglycodol, allopurinol, aluminum aspirin, methotrexate, acetyl sulfisoxazole, erythromycin, hydrocortisone, hydrocorticosterone acetate, cortisone acetate, dexamethasone and its derivatives such as betamethasone, triamcinolone, methyltestosterone, 17-S-estradiol, ethinyl estradiol, ethinyl estradiol 3-methyl ether, prednisolone, 17.varies.-hydroxyprogesterone acetate, 19-nor-progesterone, norgestrel, norethindrone, norethisterone, norethiederone, progesterone, norgesterone, norethynodrel, aspirin, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, theophylline, calcium gluconate, ketoprofen, ibuprofen, cephalexin, erythromycin, haloperidol, zomepirac, ferrous lactate, vincamine, diazepam, phenoxybenzamine, diltiazem, milrinone, capropril, mandol, quanbenz, hydrochlorothiazide, ranitidine, flurbiprofen, fenufen, fluprofen, tolmetin, alclofenac, mefenamic, flufenamic, difuinal, nimodipine, nitrendipine, nisoldipine, nicardipine, felodipine, lidoflazine, tiapamil, gallopamil, amlodipine, mioflazine, lisinolpril, enalapril, enalaprilat, captopril, ramipril, famotidine, nizatidine, sucralfate, etintidine, tetratolol, minoxidil, chlordiazepoxide, diazepam, amitriptyline, and imipramine.

The compositions of the invention include a safe and effective amount of a pharmaceutically active agent. "Safe and effective" as it is used herein, means an amount high enough to significantly positively modify the condition to be treated or the pharmaceutic effect to be obtained, but low enough to avoid serious side effects. As is mentioned herein above, compositions of the invention are considered to include both pharmaceutical agents which treat the source or symptom of a disease or physical disorder and personal care or cosmetic agents which promote bodily attractiveness or mask the physical manifestations of a disorder or disease.

Any conventional pharmaceutical permeation enhancer that does not interfere with performance of the pharmaceutically active agent can be used in the preparations according to the present invention. A "permeation enhancer" is any compound that increases the uptake of the pharmaceutically active agent. Examples of permeation enhancers which may be used with the drug delivery devices according to this invention include, without limitation, alcohols, short- and long-chain alcohols, polyalcohols, amines and amides, urea, amino acids and their esters, amides, azone or pyrrolidone and its derivatives, terpenes, fatty acids and their esters, macrocyclic compounds, sulfoxides, tensides, benzyldimethylammonium chloride, cetyl trimethyl ammonium bromide, cineole, cocamidopropyl betaine, cocamidopropyl hydroxysultaine, dodecyl pyridinium chloride, dodecylamine, hexadecyl trimethylammoniopropane sulfonate, isopropyl myristate, limonene, linoleic acid (OA), linolenic acid (LA), menthol, methyl laurate, methylpyrolidone, N-decyl-2-pyrrolidone, NLS, nicotine sulfate, nonyl-1,3-dioxolane, octyl trimethylammonium bromide, oleyl betaine, PP, polyethyleneglycol dodecyl ether, polyoxyethelene sorbitan monolaurate (TWEEN20), SLA, sodium oleate, sodium lauryl sulfate, sodium octyl sulfate (SOS), sorbitan monolaurate (S20), TWEEN20, tetracaine, and Triton X-100. Additional examples of permeation enhancers can be found in Sayani and Chien, Crit. Rev. Ther. Drug Carrier Syst. 13:85-184 (1996); Karande et al. Nature Biotechnology, 22, (2), 192-197, (2004); Pfister et al., Med Device Technol. November-December 1990; 1(6):28-33; Mitragotri, Pharm Res. November 2000; 17(11):1354-9; and Hadgraf Int J. Pharm. Jul. 5, 1999; 184(1):1-6, and references cited therein.

The drug delivery devices of the present invention are constructed in such a way that they are retained in the vagina for periods of a day up to several months and can be readily inserted and removed, for example, in the case of the human female patient. The device, due to its unique shape and size, does not obstruct the cervix, as do diaphragms. In an optional embodiment, a locally effective antimicrobial agent, for example an antibiotic such as neomycin, nystatin and polymyxin can be included within the polymeric material. The improved device of this invention possesses numerous advantages over, for example, the intravaginal devices comprising multiple reservoirs or layers. Such advantages include controlled, simultaneous release of multiple drugs, release of drugs in a substantially constant ratio over a prolonged period of time, and ease and low cost of manufacture. The drug or combination of drugs can be incorporated into the device in sufficient amounts to bring about the desired local and/or systemic effect. The drug delivery device of the present invention provides more immediate effects, as compared to existing devices, as well as more uniform and constant serum levels of drug during the predetermined period of time for which the beneficial physiologic effects are desired. This is in marked contrast to fluctuations that occur with known intravaginal devices, for example the delayed release associated with most layered devices, the inconsistent and unreliable release frequently observed with multi-compartment or multi-reservoir devices, and the variations in the pre-set fixed release ratio commonly associated with drug delivery devices for administering multiple drugs.

IV. Methods for Treating Benign Ovarian Secretory Disorders

In one embodiment, the invention relates to a method for treating benign ovarian secretory disorders in female mammals (patients) using a drug delivery device to deliver an effective amount of an LHRH composition (i.e., luteinizing hormone releasing hormone (LHRH), LHRH analogues, LHRH agonists and/or LHRH antagonists, and/or their non-peptide analogues capable of binding to the LHRH receptor), an effective amount of an estrogenic steroid and/or its receptor modulators, and an effective amount of a progestational steroid and/or its receptor modulators. Preferably, the device is administered to the patient during an induced follicular phase of the menstrual cycle, beginning, if possible, at the onset of menses. In patients whose benign ovarian secretory disorder is characterized by amenorrhea, the methods of the invention may be initiated at any time following the determination of a non-pregnant status. The continuous delivery of LHRH compositions in combination with sex steroid delivery for use in treating benign ovarian secretory disorders is described in detail in U.S. Pat. No. 5,130,137 (Crowley, Jr.), which is incorporated by reference in its entirety herein.

In addition, patients with disorders such that their ovaries malfunction for any of a variety of reasons such that their ovaries secrete excessive sex steroids, i.e., estrogens, progestins, and/or androgens, the consequences of which are recurrent irregular menstrual periods, and/or hirsutism would be included in the methods of the invention. The methods of the invention are especially useful in treating polycystic ovarian disease, and ovarian diseases characterized by dysfunctional uterine bleeding, amenorrhea, and especially hyper-, normo-, or hypo-gonadotropic amenorrhea, and hyperthecosis.

The methods of the invention for treating benign ovarian secretory disorders are characterized in that they provide a continuous hormonal replacement therapy which simulates a normal sex steroid hormone pattern in the patient that is similar to those levels and/or patterns of sex steroid secretion encountered in normal women during their ovulatory menstrual cycles.

Progesterone and estradiol are well characterized in the art. Table 1 lists current estradiol and progesterone products in human use with relevant properties. The following publications are referenced in Table 1: (1) Levy et al. Hum Reprod. March 1999; 14(3):606-10; (2) Mircuioiu et al. Eur J Drug Metab Pharmacokinet. July-September 1998; 23(3):391-6; and (3) Archer et al. Am J Obstet. Gynecol. August 1995; 173(2):471-7; discussion 477-8, all of which are herein incorporated by reference.

TABLE 1

| | Name | Steroid | Amount/Device | Rate/day | Steady State Serum Concentration | $T_{max}$ |
|---|---|---|---|---|---|---|
| Normal Menstrual Cycle Sex Steroid Secretion | | Estradiol | | 50-700 ug | 50-500 pg/ml | Midcycle |
| | | Progesterone | | | 2-5 ng/ml | Midluteal |
| Vaginal Rings | Estring | Estradiol | 2 mg | 22 ug | 8 pg/ml | 1 h |
| Intravaginal Gels | Estrace | Estradiol | 0.1 mg | | | |
| | VagiFem | | 25 ug | 25 ug | | |
| | Crinone | Progesterone | 45 & 90 mg | 45/90 mg | 7 ng/ml | 5.6-6.8 h |
| Transdermal | Alora | Estradiol | 1.5, 2.3, and 3.0 mg | 50, 75, and 100 ug | 60-100 pg/ml | 18-24 h |
| | Climara | | 2.0, 3.8, 5.7 or 7.6 mg | 25, 50, 75 or 100 ug | 22-106 pg/ml | 18-24 h |
| | Vivelle | | 0.39, 0.686, 0.78, 1.17, or 1.56 mg | 25, 37.6, 50, 75, or 100 ug | 34-104 pg/ml | 1 h |
| Oral | ORTHO-PREFEST | Estradiol | 1 mg | 1 mg/day | | 7 h |
| | Estrace | | 0.5, 1 & 2 mg | 0.5, 1 & 2 mg/day | | |
| | PROMETRIUM | Progesterone | 100/200 mg | 100/200 mg | ~3 ng/ml | 1.5/2.3 h |
| Vaginal Tablets/ Suppository | Academic Research | Progesterone | 50/100 mg | 50/100 mg | 6-7 ng/ml | 6.1/6.4 h |
| | | | 100/200 mg | 100/200 mg | 6-10 ng/mL | 4 h |
| | | | 100/200 mg | 100/200 mg | 10-14 ng/mL | |
| Our Target | WHI | Estradiol | 3 mg | 100 ug | 100 pg/mL | |
| | | Progesterone | 530 mg | 45 mg | 5 ng/mL | |
| | | D-Trp6-Pro9-Net-GnRH | 5 mg | 4 ug/Kg/day | 10-100 pg/mL | |

| | Name | Steroid | $C_{max}$ | $T_{1/2}$ | Indication |
|---|---|---|---|---|---|
| | Normal Menstrual Cycle Sex Steroid Secretion | Estradiol | 500 pg/ml | | — |
| | | Progesterone | 35 ng/ml | 12 h | |
| | Vaginal Rings | Estring | Estradiol | 63 pg/ml | | Rx of urogenitalSx in menopause |
| | Intravaginal Gels | Estrace | Estradiol | | | Rx of vulval and vaginal atrophy |
| | | VagiFem | | 50 pg/ml | | Rx of atrophic vaginitis |
| | | Crinone | Progesterone | 14 ng/ml | 34-55 h | progesterone supplementation or replacement as part of an IVF |
| | Transdermal | Alora | Estradiol | 92-144 pg/ml | 2 h | |
| | | Climara | | 32-174 pg/ml | 4 h | Rx of vaso-motor Sx. in menopause |
| | | Vivelle | | 46-145 pg/ml | 5.9-7.7 h | Rx of vulvar and vaginal atrophy |
| | Oral | ORTHO-PREFEST Estrace | Estradiol | 27.4 pg/ml | 16 h | Rx of vascometer symptoms in the menopause |
| | | PROMETRIUM | Progesterone | 17/28 ng/ml | | Prevention of endometrial hyperplasta in non-hysterectomized postmenopausal women Rx'd with estrogens |
| | Vaginal Tablets/ Suppository | Academic Research | Progesterone | 20/31 nmol/l | 13.2/13.7 h | 1 |
| | | | | 10-16 ng/mL | 9-14 h | 2 |
| | | | | 5.7-20.9 ng/mL | | 3 |
| | Our Target | WHI | Estradiol Progesterone D-Trp6-Pro9-Net-GnRH | | | |

The methods of the invention for treating benign ovarian secretory disorders comprise providing a drug delivery device having two or more segments, wherein a first segment comprising a drug-permeable polymeric substance and a LHRH, and a second segment comprising an effective amount of an estrogenic steroid or selective estrogen receptor modulator (SERM). The drug delivery device is then inserted into the vagina of the female mammal, such as a human female, to release effective amounts of the hormones. The drug-permeable polymeric substance may be a thermoplastic polymer, such as an ethylene-vinyl acetate copolymer. The drug delivery device may be in the shape of a ring, a wafer, or a suppository. In a preferred embodiment, the drug delivery device is a ring-shaped device such as the one described above in Section II.

Estrogenic steroids which can be used according to this aspect of the invention include natural estrogenic hormones and congeners, including, but not limited to, estradiol, estradiol benzoate, estradiol cypionate, estradiol valerate, estrone, piperazine, estrone sulfate, ethinyl estradiol, polyestradiol phosphate, estriol, and estrone potassium sulfate. Synthetic estrogens can be used in the invention, including, but not limited to, benzestrol, chlorotrianisene, dienestrol, diethylstilbestrol, diethylstilbestrol diphosphate, and mestranol. In the preferred embodiment of this invention, natural estrogenic hormones are used. Also included are estrogens developed for veterinary use, including equine estrogens such as equilelinin, equilelinin sulfate and estetrol.

In addition to the above-described estrogenic compounds, estrogenic steroids useful in accordance with this aspect of the invention include selective estrogen receptor modulators (SERMs), which are estrogen analogues having tissue-selective effects. Examples of suitable SERMs include tamoxifen, raloxifene, clomiphene, droloxifene, idoxifene, toremifene, tibolone, ICI 182,780, ICI 164,384, diethylstilbesterol, genistein, nafoxidine, moxestrol, 19-nor-progesterone derivatives, and 19-nor-testosterone derivatives.

Typical dose ranges for estrogenic steroids will depend upon the estrogenic steroid compounds chosen for use in the methods of the invention and the female mammal patient. As an example, for estradiol, for the human adult female, typical dose ranges will be administered such that the serum level of estradiol will be from about 20 to about 200 pg/ml. Preferably the serum level of estradiol is from about 50 to about 150 pg/ml; more preferably from about 80 to about 120 pg/ml. Levels of the synthetic estrogens which are the physiological equivalents of these ranges of estradiol can be used according to the methods of the invention.

Plasma estradiol can be measured by a variety of means well known in the art, e.g. ELISA. For example plasma estradiol levels can be measured by a microparticle enzyme immunoassay (MEIA) technology utilizing the AxSYM immunoassay system (Abbott) with the Estradiol reagent pack (Abbott, Cat. #7A63-20) according to manufacturer's protocol.

Progestational steroids which can be used according to the invention described herein include, but are not limited to, dydrogesterone, ethynodiol diacetate, hydroxyprogesterone caproate, medroxyprogesterone acetate, norethindrone, norethindrone acetate, norethynodrel, norgestrel, progesterone, and megestrol acetate.

Veterinarian progestational steroids can also be used in this invention, including acetoxyprogesterone, chlormadinone acetate, delmadinone acetate, proligesterone, melengestrol acetate, and megestrol acetate.

Other progestational steroids useful in accordance with this aspect of the invention include selective progestin receptor modulators (SPRMs). Examples of suitable SPRMs include RU486, CDB2914, 19-nor-progesterone derivatives, 19-nor-testosterone derivatives, 6-aryl-1,2-dihydro-2,2,4-trimethylquinoline derivatives, 5-aryl-1,2-dihydro-5H-chromeno[3,4-f]quinoline derivatives, 5-alkyl 1,2-dihydro-chomeno[3,4-f]quinoline derivatives, and 6-thiophenehydroquinoline derivatives.

Typical dose ranges for progestational steroids will also depend upon the progestational steroid chosen for use in this invention and upon the female mammal patient. For a human adult female, typical dose ranges will be an amount which can be administered such that the patient's serum levels of progesterone will be from about 1 to about 20 ng/ml. Preferably the serum level of progesterone is from about 1 to about 15 ng/ml; more preferably from about 2 to about 10 ng/ml.

Plasma progesterone can be measured by a variety of methods well known in the art, e.g., ELISA. For example, Levy et al. Human Reproduction, 14:606-610 (1999), which is herein incorporated by reference teaches that plasma progesterone may be measured by the IMMULITE chemiluminescent immunoassay (Diagnostic Products Corporation, Los Angeles, Calif.).

In the combined administration of an effective dose of LHRH composition, the dose range will depend upon the particular LHRH composition used, but will be in an amount sufficient to suppress LH and FSH secretion by the action of the LHRH composition on the pituitary membrane LHRH receptor and/or block its subsequent biological action. As will be understood by one of skill in the art, the effective dose ranges will be compound specific and will depend upon patient characteristics, such as species, age and weight. An effective dose range of LHRH composition may be determined by routine testing by one of skill in the art, without undue experimentation. Further, the LHRH composition may comprise one LHRH composition or may comprise two or more LHRH compositions. In general, it is expedient to administer the active LHRH composition in amounts between about 0.01 to 10 mg/kg of body weight per day. It will be understood in the art that this range will vary depending upon whether a LHRH antagonistic analogue or a LHRH agonistic analogue, or a combination of the two, is administered.

It well known in the art how to measure FSH and LH levels in plasma. For example FSH and LH can both be measured by ELISA. Levy et al. teaches that leutinizing hormone and FSH can be measured by Enzyme test kit (Boehringer Mannheim Immunodiagnostics, Sussex, UK).

As is known in the art, menstrual cycles are characteristic of humans and primates and do not occur in other vertebrate groups. Other mammals have estrous cycles. Both menstrual cycles and estrous cycles are regulated by the same interaction of the hypothalamic, pituitary and ovarian hormones, and the effects of the ovarian hormones on the reproductive tract are comparable. The menstrual cycle is generally divided into two phases: the follicular phase and the luteal phase. The follicular phase extends from the onset of menstruation to ovulation (approximately 14 days in the humans). The luteal phase extends from ovulation to the beginning of menstruation (approximately another 14 days in humans).

The estrous cycle is generally divided into four phases: the estrus phase, the metestrus phase, the diestrus phase, and the proestrus phase. Ovulation typically occurs during the estrus phase and thus the estrus and metestrus phases roughly correspond to the luteal phase. The diestrus phase and proestrus phase roughly correspond to the follicular phase. As used herein, these phases are all referred to as "follicular" and "luteal phases" of the menstrual cycle, although it is to be understood that the invention described herein also applies to mammals with estrous cycles. Appropriate dose ranges can be determined for mammals with estrous cycles by one of skill in the art through routine testing, without undue experimentation. In mammals with estrous cycles, it may also be desirable to control estrous behavior. The dose range administered for prevention of pregnancy and reduction of estrous behavior can also be determined by one of skill in the art by routine testing. The methods would be especially useful in treating, for example, female animals diagnosed with cystic ovarian disease (COD) and especially when such cysts manifest themselves as nymphomania, continuous estrus, irregular estrus, first estrus postpartum, anestrus since calving, anestrus after estrus, persistant corpus luteum or anestrus after insemination.

The methods of this invention may be administered to mammals including but not limited to humans, primates, equines, canines, felines, bovines, ovines, ursines, and fowl.

LHRH compositions are absorbed very well across a wide variety of surfaces. Thus oral, subcutaneous, intramuscular, intravenous, vaginal, nasal, transdermal and aural routes of administration have all proven to be effective. In a preferred embodiment of this invention, administration of the delivery system is made via the vaginal route. Approximately 1-10% or greater of the LHRH composition is absorbed through the vaginal epithelium. Thus, the LHRH composition is administered via a vaginal delivery system using a matrix which permits transvaginal absorption. In this same first vaginal delivery system, an effective dosage of physiological amounts of an estrogenic steroid is also delivered. This delivery system allows complete suppression of gonadotropins, removal of reproductive function of the ovaries, total suppression of ovarian steroidogenesis, and yet still effects a physiological replacement of sufficient levels of estrogen to thwart the long term side effects of the estrogen deficiency that occurs during LHRH administration. This vaginal delivery device is preferably administered during the follicular phase of the menstrual cycle, beginning at the onset of menses.

The methods of the invention would also be useful to induce breeding. In seasonal breeding animals, such as sheep, sequential application of an induced follicular phase of variable length followed by an induced luteal phase would induce subsequent estrous. Such induced estrous provides a more timely and experimentally controllable breeding. The methods of the invention would also serve to induce breeding at a higher frequency, for example, to induce breeding more than once or twice a year.

V. Methods for Preventing Pregnancy in Mammals

In another embodiment, the invention relates to a method for preventing pregnancy in a mammal. The method comprises administering an effective amount of an LHRH composition (i.e., luteinizing hormone releasing hormone (LHRH), LHRH analogues, LHRH agonists and/or LHRH antagonists, and/or their non-peptide analogues capable of binding to the LHRH receptor) and an effective amount of an estrogenic steroid and/or a selective estrogen receptor modulator (SERM) during the follicular phase of the menstrual cycle, beginning at the onset of normal menses. Next, during the luteal phase of the menstrual cycle, the method comprises administering an effective amount of a LHRH composition, an effective amount of an estrogenic steroid and/or SERM, and an effective amount of a progestational steroid and/or a selective progestin receptor modulator (SPRM). Following the luteal phase, the LHRH composition and an effective amount of an estrogenic steroid and/or SERM are administered, at which time menstruation would typically occur. The continuous delivery of LHRH compositions in combination with sex steroid delivery for use as a contraceptive is described in detail in U.S. Pat. No. 4,762,717 (Crowley, Jr.), which is incorporated by reference in its entirety herein.

The LHRH composition (i.e., luteinizing hormone releasing hormone (LHRH), LHRH analogues, LHRH agonists and/or LHRH antagonists, and/or their peptide or non-peptide analogues capable of binding to the LHRH receptor), estrogenic steroid and/or SERM, and progestational steroid or non-steroidal analogues and/or SPRM, which are useful in accordance with this aspect of the invention, are described above.

Typical dose ranges for estrogenic steroids and SERMs will depend upon the estrogenic steroid compound chosen for use in this invention and the female mammal patient. For a human adult female, typical dose ranges will be administered such that the serum level of estradiol will be from about 50 to about 140 pg/ml. Preferably the serum level of estradiol is from about 20 to about 150 pg/ml; more preferably from about 80 to about 120 pg/ml. Serum estrogenic steroid levels can be measured as described in Section IV.

Typical dose ranges for progestational steroids and SPRMs will also depend upon the progestational steroid chosen for use in this invention and upon the female mammal patient. For a human adult female, typical dose ranges will be an amount which can be administered such that the patient's serum levels of progesterone will be from about 1 to about 20 ng/ml. Preferably the serum level of progesterone is from about 1 to about 15 ng/ml; more preferably from about 2 to about 10 ng/ml. Serum progesterone levels can be measured as described in Section IV.

In the combined administration of an effective dose of LHRH composition, the dose range will depend upon the particular LHRH composition used, but will be in an amount sufficient to suppress LH and FSH secretion by the action of the LHRH composition on the pituitary membrane receptor and block its subsequent actions. As will be understood by one of skill in the art, the effective dose ranges will be compound specific and will depend upon patient characteristics, such as age and weight. An effective dose range of LHRH composition may be determined by routine testing by one of skill in the art, without undue experimentation. Further, the LHRH composition may comprise one LHRH composition or may comprise two or more LHRH compositions. In general, it is expedient to administer the active LHRH composition in amounts between about 0.01 to 10 mg/kg of body weight per day. It will be understood in the art that this range will vary depending upon whether a LHRH antagonistic analogue or a LHRH agonistic analogue, or a combination of the two, is administered. Serum LH and FSH levels can be measured as described in Section IV.

As is known in the art, menstrual cycles are characteristic of humans and primates and do not occur in other vertebrate groups. Other mammals have estrous cycles. Both menstrual cycles and estrous cycles are regulated by the same interaction of the hypothalmic, pituitary and ovarian hormones, and the effects of the ovarian hormones on the reproductive tract are comparable. The menstrual cycle is generally divided into two phases: the follicular phase and the luteal phase. The follicular phase extends from the onset of menstruation to ovulation (approximately 14 days in humans). The luteal phase extends from ovulation to the beginning of menstruation (approximately another 14 days in humans).

The estrous cycle is generally divided into four phases: the estrus phase, the metestrus phase, the diestrus phase, and the proestrus phase. Ovulation typically occurs during the estrus phase and thus the estrus and metestrus phases roughly correspond to the luteal phase. The diestrus phase and proestrus phase roughly correspond to the follicular phase. As used herein, these phases are all referred to as follicular and luteal phases of the menstrual cycle, although it is to be understood that the inventions described herein also apply to mammals with estrous cycles. Appropriate dose ranges can be determined for mammals with estrous cycles by one of skill in the art through routine testing, without undue experimentation. In mammals with estrous cycles, it may also be desirable to control estrous behavior. The dose range administered for prevention of pregnancy and reduction of estrous behavior can also be determined by one of skill in the art by routine testing.

The method of this invention may be administered to mammals including but not limited to humans, primates, equines, canines, felines, bovines, and ursines.

The methods of the invention for preventing pregnancy in a mammal comprise providing a drug delivery device having two or more segments, wherein a first segments comprising a drug-permeable polymeric substance and a LHRH, and a second segment comprising an effective amount of an estrogenic steroid or SERM. The drug delivery device is then inserted into the vagina of the female mammal, such as a human female, to release effective amounts of the hormones. The drug-permeable polymeric substance may be a thermoplastic polymer, such as an ethylene-vinyl acetate copolymer. The drug delivery device may be in the shape of a ring, a wafer, or a suppository. In a preferred embodiment, the drug delivery device is a ring-shaped device such as the one described below in Section V.

In one embodiment of this aspect of the invention, the device described above is removed following maintenance of the LHRH/estrogenic steroid delivery system during the follicular phase (typically fourteen days in humans), and replaced by a second vaginal delivery system which has the LHRH/estrogenic steroid combination and the effective physiological amount of a progestational steroid or SPRM. This second delivery system is administered during the luteal phase of the menstrual cycle (typically fourteen days in humans), until the onset of normal menses. This second delivery system provides an artificial luteal phase to the female.

Following the second vaginal delivery system, and readministration of the first vaginal delivery system, menstruation occurs, reassuring the patient of lack of conception. Further, the administration of a progestational steroid in the second delivery system permitting menstruation, also avoids endometrial hyperplasia.

In an alternate embodiment of this aspect of the invention, the two formulations described above (the LHRH/estrogenic steroid formulation and LHRH/estrogenic/progestational steroid formulation) are combined in one drug delivery device, which is designed to remain in the vagina of the female for the entire menstrual cycle. In this embodiment, the drug delivery device comprises at least one cylindrical unitary segment per hormonal formulation, or, alternatively, at least one cylindrical unitary segment per active ingredient (i.e., LHRH, sex steroid, or sex steroid modulator). The choice of polymeric material and the ratio of polymeric material to LHRH/sex steroid/sex steroid modulator are preselected for each segment to provide the appropriate release kinetics for the individual steroids and/or steroidal formulations. By selecting the polymeric material based on its release properties and adjusting the ratio of polymeric material to drug, the method of the present invention provides the pre-set timed delivery of LHRH, estrogenic steroid, and progestational steroid at the appropriate phase of the menstrual cycle to achieve the desired contraceptive effect. For example, this "combined" device would release LHRH and/or its agonists or antagonists continuously for 30 days in combination with an estrogenic compound. After approximately two weeks of such therapy, the device would release progesterone or a progestational steroid or non-steroidal compound for the last 14 days of the cycle following which its declining levels would induce a menstrual bleed due to decreasing progesterone support exactly as occurs in the normal female menstrual cycle. In one embodiment, the two formulations described above (the LHRH/estrogenic steroid formulation and LHRH/estrogenic/progestational steroid formulation) would exhibit the characteristics described in Table II.

TABLE II

| Drug | Drug Circulation Level | Release from the Ring per day | Drug Loading for 21 days of Release |
|---|---|---|---|
| Ring A | | | |
| Estradiol | 100 pg/mL | 100 µg | 2.1 mg |
| D-Trp6-Pro9-Net-GnRH | 10-100 pg/mL | 4 µg/Kg | 5 mg |
| Ring B | | | |
| Estradiol | 100 pg/mL | 100 µg | 2.1 mg |
| Progesterone | 6 ng/mL | 45 mg | 630 mg |
| D-Trp6-Pro9-Net-GnRH | 10-100 pg/mL | 4 µg/Kg | 5 mg |

VI. Hormone Replacement Therapy

In another aspect, the invention relates to a method for treating perimenopausal or postmenopausal women, including women of all ages having premature ovarian failure (e.g., young women who have had an ablation of ovarian function due to surgery, radiation, or chemotherapy). In this aspect, the invention provides methods for treating a decrease in estrogen secretion as well as relieving the symptoms and signs associated with menopausal, perimenopausal, and postmenopausal periods in women. In one embodiment, the method involves providing a drug delivery device, as described in Section V below, comprising a drug-permeable polymeric substance and (i) an androgen or a selective androgen receptor modulator (SARM), (ii) an estrogen or a selective estrogen receptor modulator (SERM), and (iii) a progestin or a selective progestin receptor modulator (SPRM) or any combination of the above depending upon the individual patient's needs. The drug delivery device is inserted into the vagina of the woman to release an effective amount of the sex steroids or sex steroid modulators to the woman. The continuous delivery of replacement hormones for treating perimenopausal or postmenopausal women is described in detail in U.S. Ser. No. 09/585,935, filed Jun. 2, 2000 (K. A. Martin et al.), which is incorporated by reference in its entirety herein.

In another embodiment, the method of the present invention involves providing a drug delivery device, as described below, comprising a drug-permeable polymeric substance and (i) a SERM and (ii) an androgen or a SARM. Optionally, the drug delivery device also includes (iii) a progestin or a SPRM. The drug delivery device is inserted into the vagina of the woman, where it releases a therapeutically effective amount of the active agents (SERM, an androgen or SARM, and optionally a progestin or SPRM), thereby relieving the symptoms and signs associated with the menopausal, perimenopausal and postmenopausal periods.

In yet another embodiment, the method of the present invention involves the use of a drug delivery device comprising (i) a SERM and (ii) an estrogen, and optionally (iii) a progestin or SPRM. The drug delivery device is inserted into the vagina of the woman, where it releases a therapeutically effective amount of the active agents (SERM, estrogen, and optionally progestin or SPRM), thereby relieving the symptoms and signs associated with the menopausal, perimenopausal and postmenopausal periods.

In another variation of the above, the drug delivery device contains (i) a SERM, (ii) an estrogen, and (ii) an androgen or SARM, and optionally (iv) a progestin or SPRM. The drug delivery device is inserted into the vagina of the woman, where it releases a therapeutically effective amount of the active agents (SERM, estrogen, androgen or SARM, and optionally progestin or SPRM), thereby relieving the symptoms and signs associated with the menopausal, perimenopausal and postmenopausal periods.

Virtually all postmenopausal and perimenopausal women can be treated with the methods of the invention with or without the addition of LHRH or one of its peptide or non-peptide analogues. If desired, such a woman can be identified as being in need of hormone replacement therapy (using standard criteria, as described, for example, by the American College of Physicians Guidelines, which is incorporated herein by reference) prior to treatment of the woman with the methods of the invention. A variety of therapeutic regimens are suitable for use in the invention, and practitioners of ordinary skill in the art can readily optimize a particular regimen for a particular woman by monitoring the woman for signs and symptoms of hormone deficiency, and increasing or decreasing the dosage and/or frequency of treatment as desired.

In this embodiment of the invention, the androgen is administered at a daily dosage of 0.01 µg to 5 mg/kg of body weight (e.g., 1 µg/kg to 5 mg/kg), the estrogen typically is administered at a dosage of 0.01 µg/kg to 4 mg/kg (e.g., 0.2 µg/kg to 100 µg/kg), and the progestin typically is administered at a dosage of 0.02 mg/kg to 200 mg/kg (e.g., 2 µg/kg to 10 mg/kg). A SARM typically is administered at a daily dosage of 0.01 µg/kg to 100 mg/kg of body weight (e.g., 1 µg/kg to 4 mg/kg), a SERM typically is administered at a dosage of 0.01 µg/kg to 100 µg/kg (e.g., 1 µg/kg to 2 mg/kg), and a SPRM typically is administered at a dosage of 0.01 µg/kg to 100 mg/kg (e.g., 1 µg/kg to 30 mg/kg). Typically, the woman will be treated over the course of several months or years, or even life-long to ameliorate the signs and symptoms resulting from natural or induced impairment of ovarian function.

In one example of a suitable method of treating perimenopausal women, the therapeutic regimen entails administering to the woman a drug delivery device comprising each of (i) an androgen or SARM, (ii) an estrogen or SERM, and (iii) a progestin or SPRM for 13 to 14 days, followed by administering each of (i) an estrogen or SERM and (ii) an androgen or SARM for 13 to 14 days. The dosages listed above are suitable. In this embodiment, the drug delivery device is removed following the initial 13-14 day period (the follicular phase), and replaced by a second drug delivery device containing the estrogen or SERM and androgen or SARM combination. Alternatively, the two formulations (the androgen/SARM, estrogen/SERM and progestin/SPRM formulation; and the estrogen/SERM and androgen/SARM formulation) are combined in a single drug delivery device, which is designed to remain in the vaginal tract of the female for the entire menstrual cycle, as described above in Section III in the context of contraception.

In one example of a suitable method of treating menopausal women, the therapeutic regimen entails administering to the woman a drug delivery device comprising each of (i) an androgen or SARM, (ii) an estrogen or SERM, and (iii) a progestin or SPRM. The dosages listed above are suitable. In this embodiment, the drug delivery device is designed to remain in the vaginal tract of the patient for at least 30 days, preferably several months (e.g., 2-4 months).

In another method, the woman is treated with a drug delivery device containing each of (i) a SERM, (ii) an androgen or SARM, and, optionally, (iii) a progestin or SPRM. In a typical therapeutic regimen, the device remains in the vaginal tract of the woman for at least 30 days, delivering a daily dose of active agents at the dosages listed above. Usually, the woman will be treated over the course of several months or years, or even life-long to relieve her of the signs and symptoms resulting from natural or induced impairment of ovarian function.

Alternatively, the woman can be treated with a drug delivery device containing each of (i) a SERM and (ii) an estrogen, and, optionally, (iii) a progestin or SPRM. In a typical therapeutic regimen, this combination of steroids is administered to the woman for at least 30 days at the daily dosages listed above. Usually, the woman will be treated over the course of several months or years, or even life-long to relieve her of the signs and symptoms resulting from natural or induced impairment of ovarian function.

In still an alternative method, the woman can be treated with a drug delivery device containing each of (i) a SERM, (ii) an estrogen, (iii) an androgen or SARM, and, optionally, (iv) a progestin or SPRM. In a typical therapeutic regimen, this combination of steroids is administered to the woman for at least 30 days at the daily dosages listed above. Usually, the woman will be treated over the course of several months or years, or even life-long to relieve her of the signs and symptoms resulting from natural or induced impairment of ovarian function.

For long-term delivery of replacement hormones, the device will typically contain sufficient quantities of the sex steroids or sex steroid modulators to provide a 1 to 48 month supply, a 1 to 36 month supply, a 1 to 24 month supply, preferably a 1 to 12 month supply, and most preferably a 1 to 6 month supply of replacement hormones.

The following examples are merely illustrative of the present invention and they should not be considered as limiting the scope of the invention in any way, as these examples and other equivalents thereof will become apparent to those versed in the art in the light of the present disclosure, drawings and the accompanying claims. For example, the following examples illustrate the practice of the invention for controlled release of progesterone, estradiol, and LHRH or gonadotropin releasing hormone (GnRH). As described elsewhere herein, the invention is useful in a wide variety of applications and for treating numerous conditions and disorders. Thus, as will be appreciated by those skilled in the art, drug delivery devices according to the invention can be manufactured to contain any number of segments or rods, comprising any suitable drug or drug combination, and may be used to treat a variety of indications, in both male and female mammals.

EXAMPLES

Example 1

Preparation of a Vaginal Ring for Controlled Release of Progesterone, Estradiol and Gonadotropin Releasing Hormone (GnRH)

The intravaginal drug delivery device illustrated in FIG. 1 was prepared using poly(ethyl-co-vinyl acetate) (EVA) manufactured by Aldrich Chemical Co. (Cat. No. 34,050-2; Lot No. 07322DR). 630 (milligrams) mg of progesterone (Sigma Corp.; Cat. No. P-3972) or 2.8 mg of estradiol (Sigma Corp.; Cat. no. E-1072) were each dissolved separately in approximately 5 mL of dichloromethane (Fluka Chem. Co.; Cat. No. 66740; Lot No. 404915/1 62800) in separate scintillation vials. Next, polymeric mixtures were prepared by adding 1400 mg of EVA to the progesterone solution and 1800 mg of EVA to the estradiol solution, and mixing the EVA/drug compositions using a rotary shaker. The resulting mixtures were then solvent cast in dry ice using ethanol as the solvent (Pharmco; Cat. No. 111 USP 200 CSGL; Lot No. M8241). The solvent was allowed to evaporate overnight, and the dry EVA/drug mixtures were then ground into powders. The EVA/drug powders were placed in an injection molding unit (DSM, Geleen, Holland). The injector was heated to approximately 80° C. The molten EVA/drug compositions were extruded into stainless steel mold (the mold is at 10° C.), creating a 1800 mg ring with an outer diameter of 50 mm and a cross section of 4 mm.

Similarly, a polymeric ring comprising GnRH agonist (D-Trp6-Pro9-Net-GnRH) was prepared by dissolving 10 mg of GnRH agonist and 450 mg of methyl cellulose in approximately 5 mL methylene chloride. 1800 mg EVA was added. The EVA/drug mixture was dried and the resulting powder was placed in an injection molding unit (DSM, Geleen, Holland). The injector was heated to approximately 80° C. The molten EVA/GnRH/cellulose compositions was extruded into stainless steel mold (the mold is at 10° C.), creating a 1800 mg EVA ring with an outer diameter of 50 mm and a cross section of 4 mm.

The EVA rings containing estradiol, progesterone, and GnRH were each aseptically cut into unitary cylindrical segments of the appropriate lengths, i.e., lengths that contain sufficient quantities of drug to provide therapeutically effective amounts of each drug. The pieces of the EVA loaded drug were placed back in the mold and neat EVA was injected to the mold to connect the pieces together. If needed, a fourth (placebo) segment of EVA may be used to complete the ring structure.

The vaginal ring described herein was designed to deliver 21-day dosages of each drug, i.e., 100 micrograms (μg) per day of estradiol, 6 milligrams (mg) per day of progesterone, and 240 μg per day of GnRH.

Example 2

Intravaginal Administration of GnRH to Rhesus Monkeys

Compositions comprising GnRH were prepared using an over-the-counter hydrogel sold under the name Replens® (Columbia Laboratories, Inc., Livingston, N.J.). Compositions comprising GnRH were prepared by mixing 10 mg of GnRH with 2 g of Replens®. 2 g of the GnRH/Replens® mixture was then placed in the vaginal tracts of five Rhesus monkeys and allowed to remain there for 9 hours. Blood samples were obtained at one hour intervals for the full 9 hour course. The blood samples had the serum separated from the clot by centrifugation and samples were subjected to an RIA assay to measure GnRH. GnRH levels were determined based on a traditional double antibody RIA for GnRH (this protocol can be modified to also measure GnRH agonists, or GnRH antagonists by varying the antibody).

Figure 2:
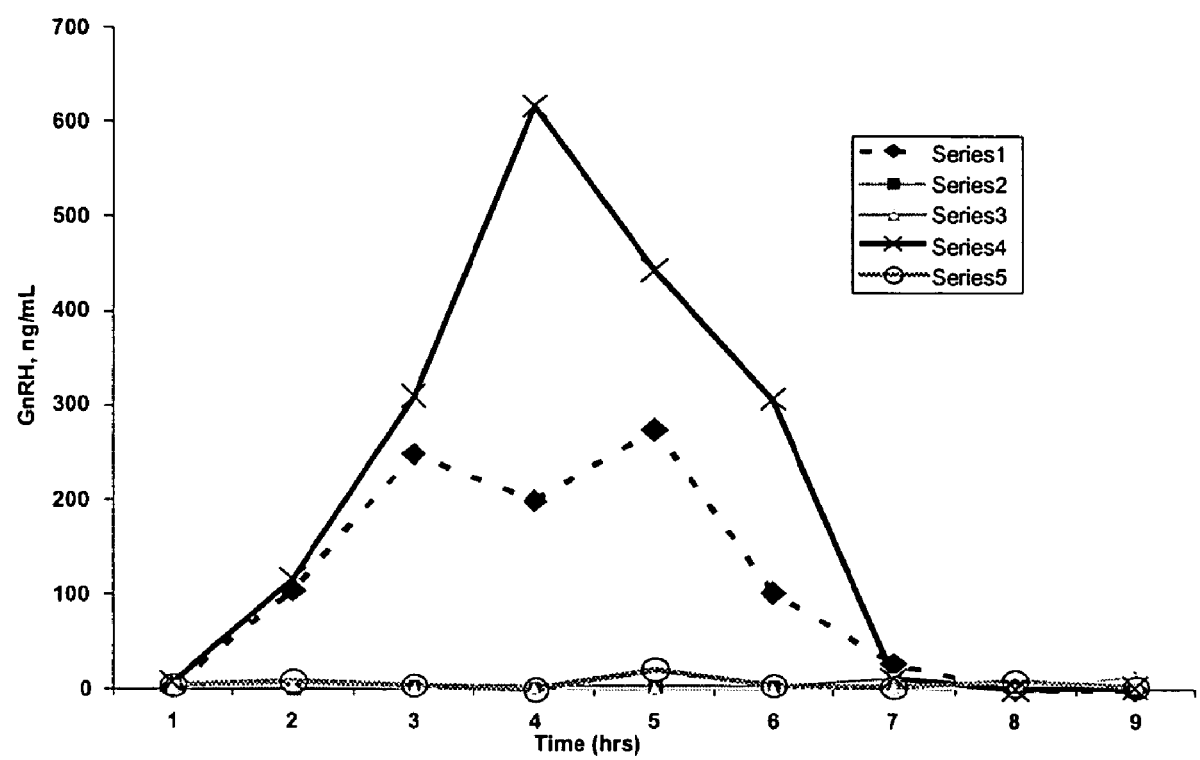
FIG. 2 illustrates the serum level (ng/ml) of gonadotropin releasing hormone (GnRH) in Rhesus monkeys following vaginal administration of a composition comprising GnRH and a commercially available hydrogel (Replenz®)

Briefly, anti-GnRH was added to standard and test samples and incubated at room temperature for 20-24 hours. The 1-125 labeled GnRH were diluted to 21,000-22,5000 CPM/100 μl solutions and added to each tube of the assay and to total count tubes and incubated at room temperature for 20-24 hours. 100 μl of sheep anti-rabbit gamma globulin (SARGG) and 100 μl of 16% PEG (Fisher, Cat. # P156-500) was added to each tube and incubated at 4° C. for 1 hour. Samples were washed with 2 ml of distilled water and centrifuged at 3000 rpm for 20 minutes. Supernatants were decanted and pellets were counted for one minute in a gamma counter. FIG. 2 shows the serum levels of GnRH in three monkeys as a function of time.

This example shows that GnRH (molecular weight of approximately 1,100) can traverse the vaginal epithelium in primates in sufficient quantities to achieve therapeutic serum levels of the hormone.

Example 3

Simultaneous Release of Estradiol, Progesterone, GNRH from an EVA Ring

Intravaginal drug delivery devices comprising estradiol, progesterone, and GnRH were prepared as described in Example 1. Estradiol, progesterone and GnRH rings were placed in 100 ml of release media (70:30 PBS:EtOH, pH=6) at 37° C. on as rotary shaker (100 RPM). At the indicated time points media was collected and measured by HPLC on an Agilent 1100 Series HPLC (Agilent, Forest City, Calif.). Estradiol and progesterone were detected by UV at 230 nm while GnRH was measured at 215 nm. Results were calculated based on the area under the curve compared to a 5 point calibration curve. Results were expressed as the cumulative release in μg released over the course of the experiment.

Figure 3:
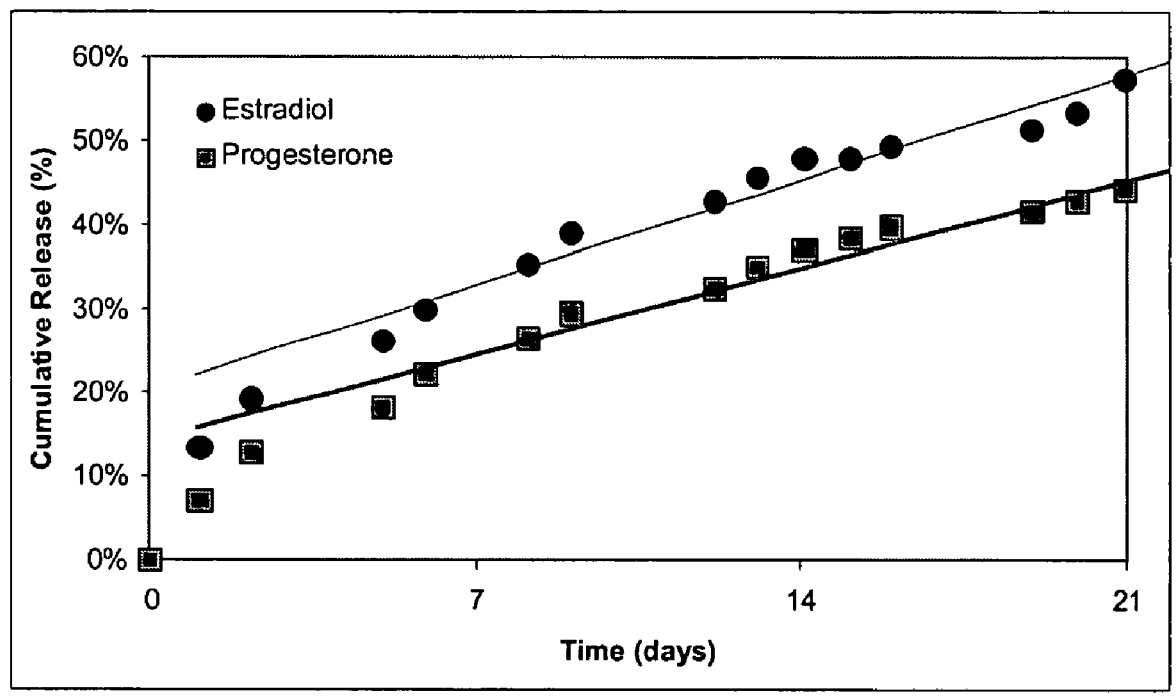
FIG. 3 illustrates the in vitro zero order release kinetics of estradiol (circles) and progesterone (squares) from an EVA-based intravaginal delivery device of the invention.
Figure 4:
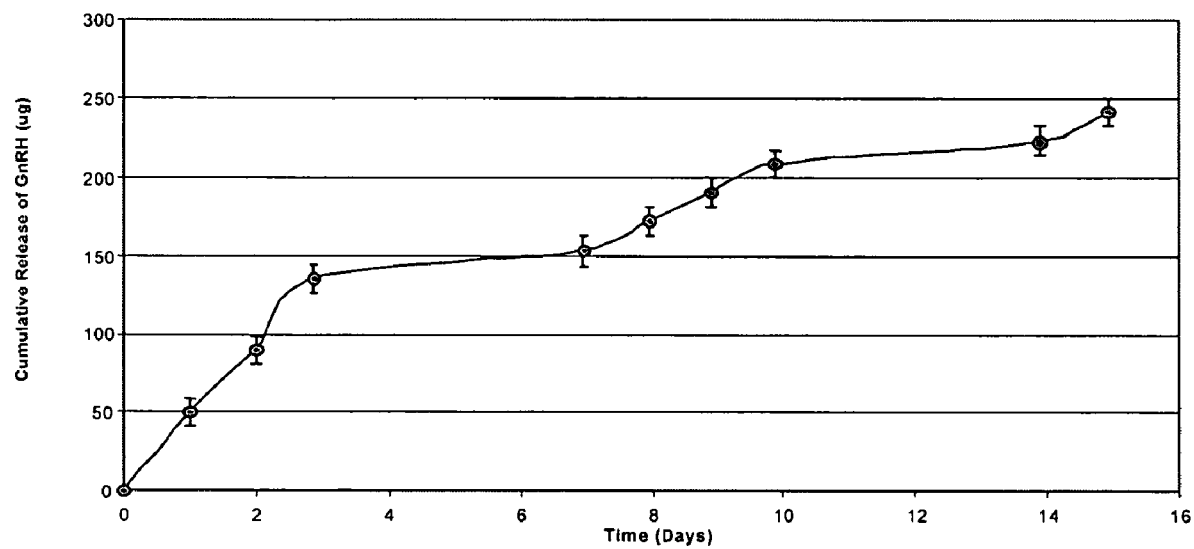
FIG. 4 illustrates the in vitro zero order release kinetics of natural GnRH from an EVA-based intravaginal delivery device of the invention.

FIG. 3 shows the in vitro zero order kinetic release of estradiol and progesterone over a 21-day period. FIG. 4 shows the in vitro zero order kinetic release of GnRH during this same period.

This example demonstrates stable zero order release kinetics for estradiol, progesterone, and GnRH over a 14 to 21 day period, without drug interactions or interference. The example also shows that vaginal rings produced in accordance with the present invention have sufficient capacity to sustain at least 21 days of adequate flux rates of GnRH (i.e., delivery rates capable of producing a serum level of 3-6 ng/ml in the circulation) to completely silence ovarian production of sex steroids, thereby totally suppressing ovulation. The vaginal rings also have sufficient capacity to deliver therapeutically effective amounts of the naturally secreted ovarian hormones, estradiol and progesterone, to restore both normal levels and patterns of each and to produce a normal, monthly menstrual flow. Natural estradiol should be administered at a rate of 100 μg/day, whereas progesterone should be delivered at approximately 45 mg/day, i.e., rates that have been demonstrated to produce serum levels of approximately 100 pg/ml of estradiol and 6,000 μg/ml/day of progesterone.

Example 4

Release Kinetics of Estradiol and Progesterone from an EVA Matrix

EVA mixtures containing estradiol and progesterone where prepared as described in Example 1 above, except that the EVA/drug mixtures were not further processed by injection molding or extrusion to form rings. After drying, the compositions (discs) were evaluated for their release kinetics. Estradiol and progesterone were placed in 100 ml of release media (70:30 PBS:EtOH, pH=6) at 37° C. on a rotary shaker (100 RPM). At the indicated time points, media was collected and measured by HPLC on an Agilent 1100 Series HPLC (Agilent, Forest City, Calif.). Estradiol and progesterone were detected by UV at 230 nm. Results were calculated based on the area under the curve compared to a 5 point calibration curve. Results are shown in FIG. 5.

Figure 5:
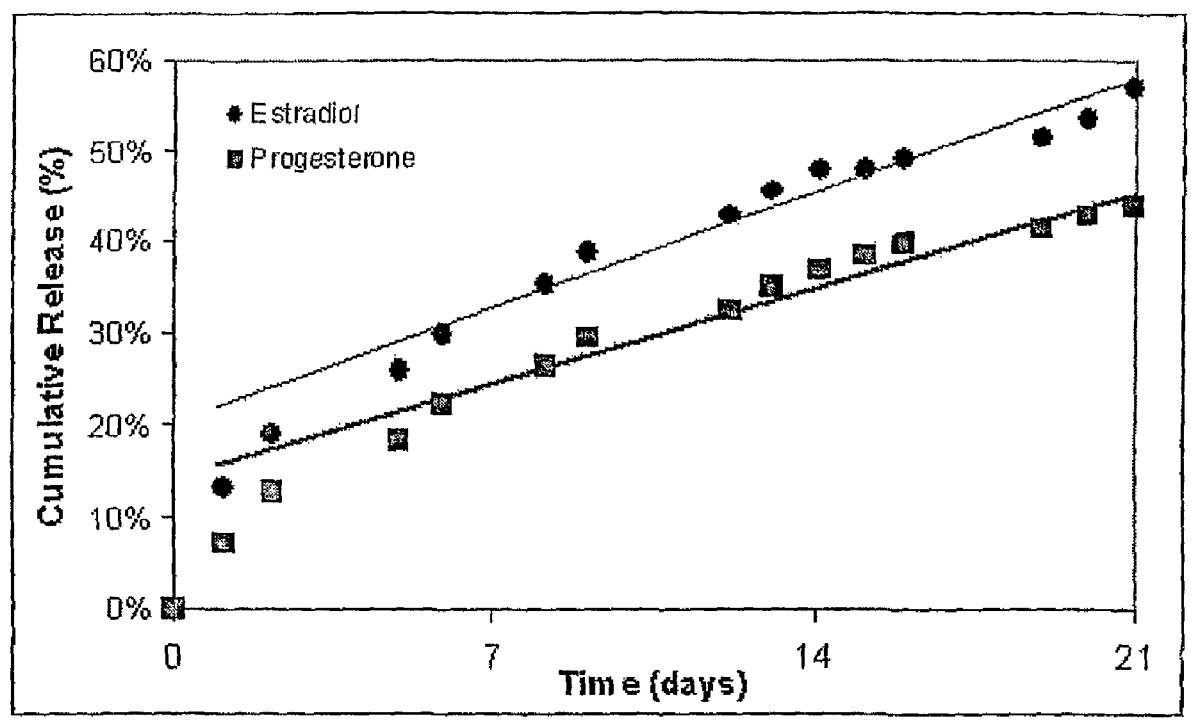
FIG. 5 illustrates the bi-phasic release kinetics of estradiol (circles) and progesterone (squares) from EVA-based delivery devices.

As shown in FIG. 5, the dry EVA/drug mixtures provide bi-phasic release kinetics with a total recovery of 70% over a 21-day period.

Example 5

Effect of Cellulosics on Release Kinetics

Figure 6:
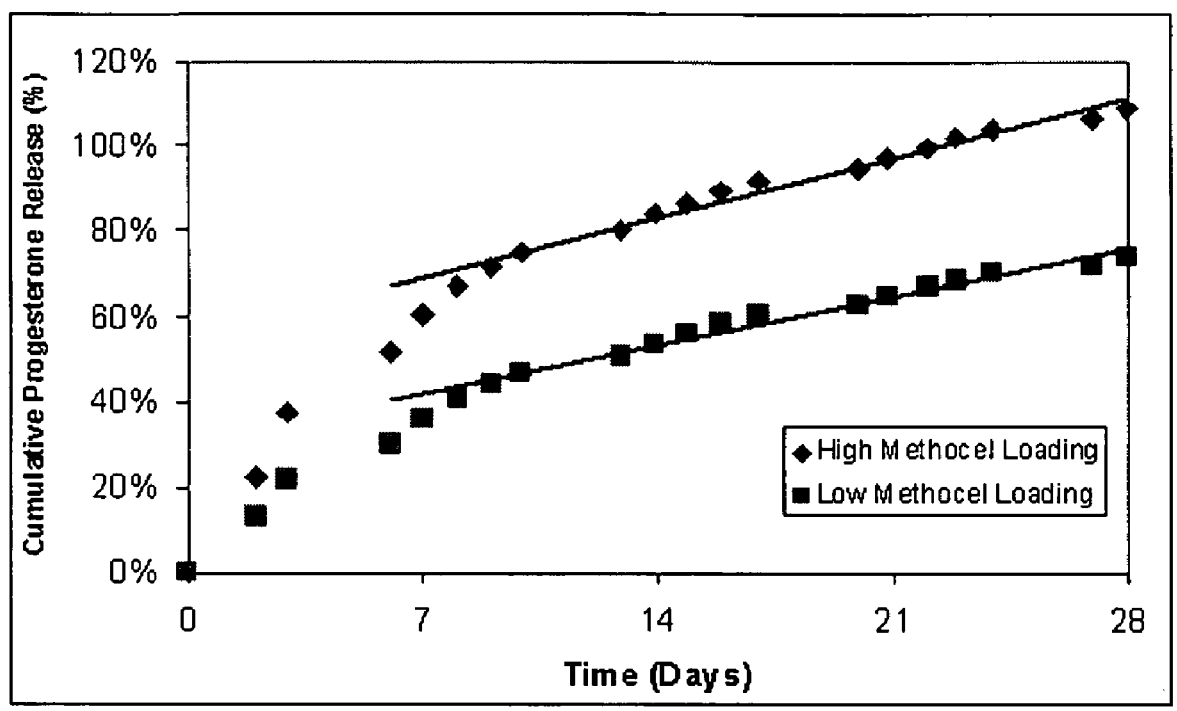
FIG. 6 illustrates the effect of cellulosics on the release kinetics of progesterone from an EVA-based delivery device, where high concentrations of ethocel are represented by diamonds and low concentrations of ethocel are represented by squares.

EVA mixtures containing progesterone and estradiol where prepared as described in Example 1 above, except that the EVA/drug mixtures were not further processed by injection molding or extrusion. Also, varying amounts of a commercially available cellulosic, Methocel® (Dow Chemicals, Co., Midland, Mich.) were incorporated into the mixtures to evaluate the effect of cellulosics on release kinetics. Briefly, estradiol and progesterone were each dissolved in two separate vials of ethanol, and a low concentration (5% by weight) and a high concentration (25% by weight) of Methocel® was added to the estradiol and progesterone vials. The solutions were slowly emulsified into a methylene chloride solution containing EVA. The resulting emulsions were solvent-casted into a mold, which was then cooled on dry ice. Following sublimation, the solvents were cut into 1 cm×1 cm samples, and placed in scintillation vials, to which 0.1 M phosphate buffered saline (pH 6.10) and ethanol were added in a 70:30 ratio. The vials were placed in a 37° C. incubator on a shaker rotating at 100 RPM. The buffer solution was replaced at predetermined time points. The released amount of estradiol and progesterone was determined by UV/VIS spectrophotometry at 280 nm or 250 nm, respectively. Next, the release kinetics were determined by plotting the cumulative release amounts as a function of time. As shown in FIG. 6, the addition of Methocel® results in pseudo zero order release kinetics. Also, the higher the ratio of cellulosics to progesterone, the greater the release rate of progesterone. This example demonstrates that the release rate of a drug from the drug delivery device can be manipulated through the use of excipients, such as cellulosics.

Example 6

Release Kinetics of Estradiol and Progesterone from an EVA Matrix

Figure 7:
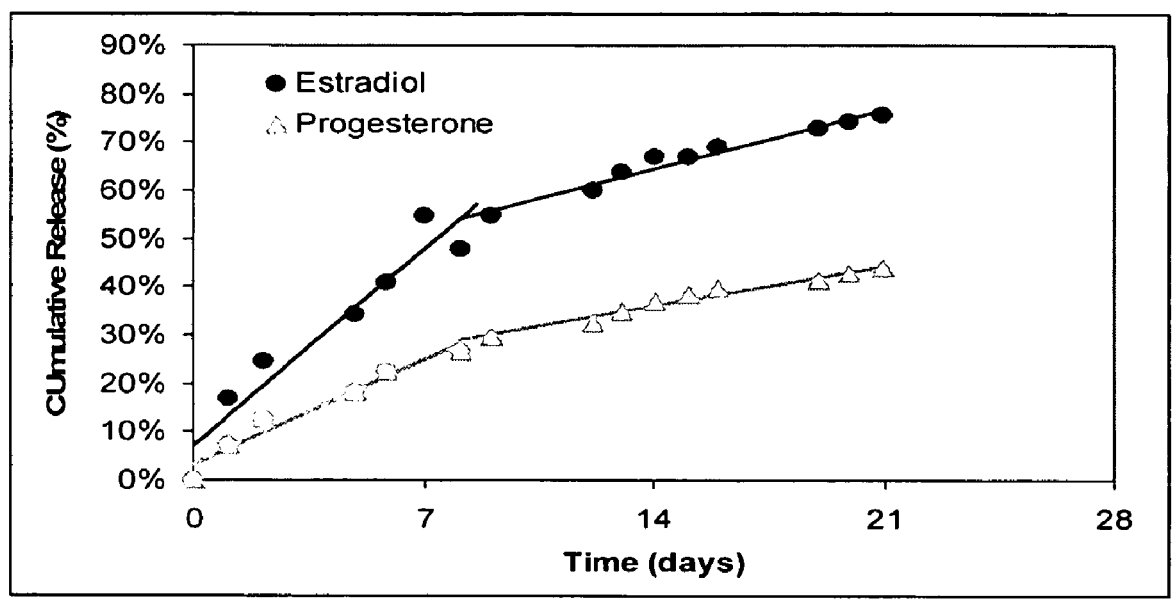
FIG. 7 illustrates the bi-phasic release kinetics of estradiol (circles) and progesterone (squares) from a single EVA-based delivery device.

EVA mixtures containing estradiol and progesterone were prepared as described in Example 1 above, except that the EVA/drug mixtures were not further processed by injection molding or extrusion. Also, the EVA/drug mixtures were combined to form a double-sided disc, comprising estradiol on one side and progesterone on the other. After drying, the discs were evaluated for their release kinetics. Briefly, Estradiol and progesterone were placed in 100 ml of release media (70:30 PBS:EtOH, pH=6) at 37° C. on as rotary shaker (100 RPM). At the indicated time points, 100% of the media was collected for measurement and 100 ml of release media was replaced. The media was measured by an Agilent 1100 Series HPLC (Agilent). Estradiol and progesterone were detected by UV at 230 nm. Results were calculated based on the area under the curve compared to a 5 point calibration curve and depicted in FIG. 7 as the cumulative percent released. As shown in FIG. 7, estradiol and progesterone have independent bi-phasic release kinetics.

Example 7

Intravaginal Administration of GnRH to Rhesus Monkeys

Polymeric mixtures comprising GnRH and a polyacrylic (polycarbophyl) based hydrogel, sold under the tradename Replens® (LDS Consumer Products, Cedar Rapids, Iowa), were prepared by mixing 10 mg of GnRH with 2 g of hydrogel (0.5% wt/wt; pH 7). 2 g aliquots of the GnRH/hydrogel mixture were then placed in the vaginal tracts of five Rhesus monkeys and allowed to remain there for 48 hours. Blood samples were taken at the specified intervals of time an assayed for GnRH and LH levels.

Figure 8:
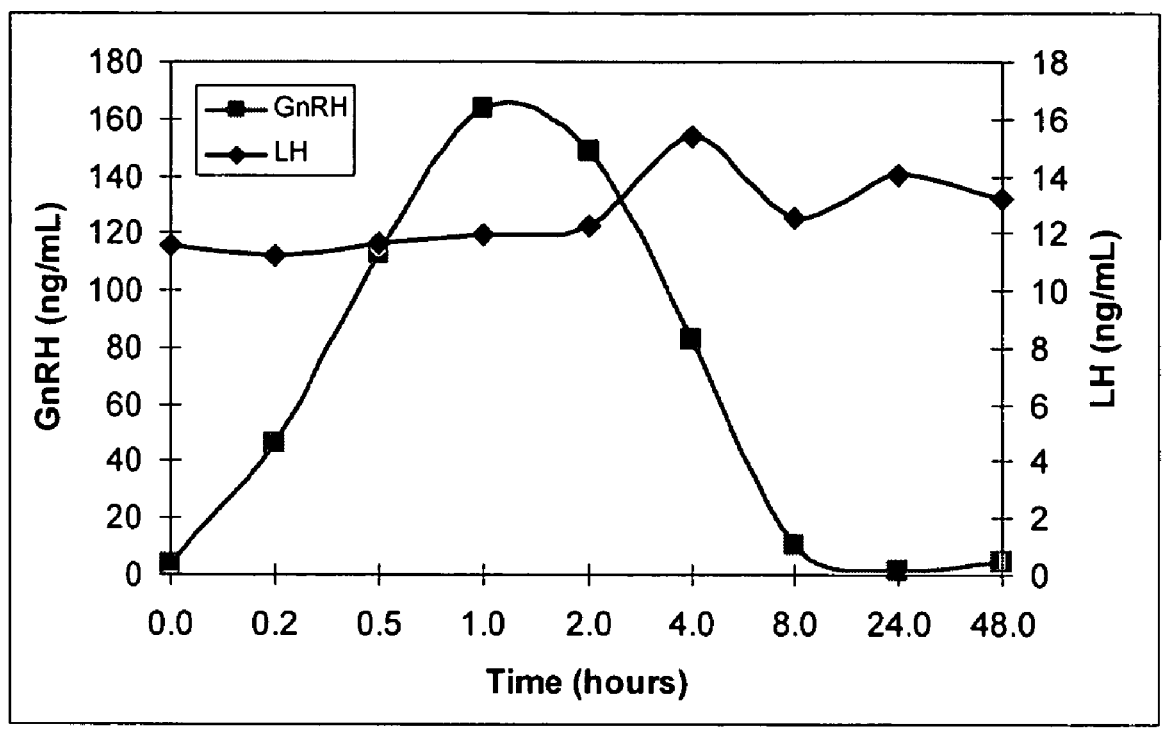
FIG. 8 illustrates the pharmacokinetics of intravaginally administered GnRH in Rhesus monkeys and the corresponding effect on endogenous levels of luteinizing hormone (LH, diamonds)

Briefly, anti-GnRH was added to standard and test samples and incubated at room temperature for 20-24 hours. The 1-125 labeled GnRH were diluted to 21,000-22,5000 CPM/100 ul solutions and added to each tube of the assay and to total count tubes and incubated at room temperature for 20-24 hours. 100 ul of sheep anti-rabbit gamma globulin (SARGG) and 100 ul of 16% PEG (Fisher, Cat. # P156-500) was added to each tube and incubated at 4° C. for 1 hour. Samples were washed with 2 ml of distilled water and centrifuged at 3000 rpm for 20 minutes. Supernatants were decanted and pellets were counted for one minute in a gamma counter. Results were expressed as ng/ml of GnRH and LH. FIG. 8 shows the serum levels of GnRH (mean level in diamonds) in the monkeys as a function of time, as well as the corresponding serum levels of endogenous luteinizing hormone (LH) (mean level in squares).

This example demonstrates sufficient transvaginal absorption of GnRH to provide ng/mL quantities of GnRH in the serum. As expected, the release of exogenous GnRH produces elevated levels of endogenous LH, thus demonstrating the biological activity of the GnRH.

Example 8

Formation of a Multi-Linked Ring

Figure 9:
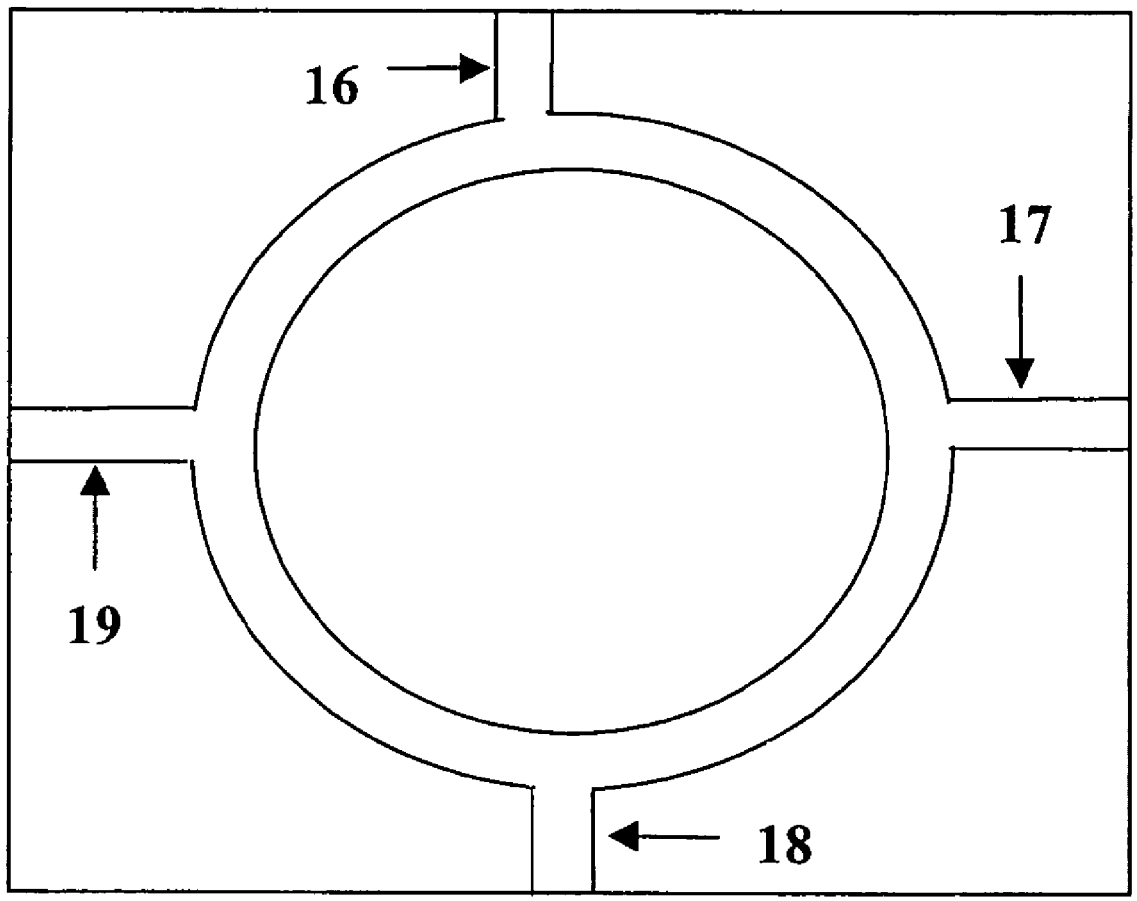
FIG. 9 shows a ring-shaped multiple port mold consisting of a Portal No. 1, Portal No. 2, Portal No. 3, and Portal No. 4.

The multi-linked intravaginal drug delivery device illustrated in FIG. 9 can be prepared using poly(ethyl-co-vinyl acetate) (EVA) manufactured by Aldrich Chemical Co. (Cat. No. 34,050-2; Lot No. 07322DR). 630 (milligrams) mg of progesterone (Sigma Corp.; Cat. No. P-3972), and 3.0 mg of estradiol (Sigma Corp.; Cat. no. E-1072) can be dissolved separately in approximately 5 mL of dichloromethane (Fluka Chem. Co.; Cat. No. 66740; Lot No. 404915/1 62800) in separate scintillation vials. Next, polymeric mixtures can be prepared by adding 1000 mg of EVA to the progesterone solution and 300 mg of EVA to the estradiol solution, and mixing the EVA/drug compositions using a rotary shaker. Similarly, a mixture comprising GnRH agonist (2.5 mg (D-Trp6-Pro9-Net-GnRH), 110 mg of methyl cellulose and 50 mg of EVA) can be prepared by dissolving the mixture in 5 mL methylene chloride.

The resulting mixtures can then be individually solvent cast in dry ice using ethanol as the solvent (Pharmco; Cat. No. 111 USP 200 CSGL; Lot No. M8241). The solvent can be evaporated overnight, and the dry EVA/drug mixtures can be ground into powders. The EVA/drug powders can be placed in individual injection molding units (DSM, Geleen, Holland) and injected at 80° C. into the multiport molding of FIG. 9. For example, the Portal No. 1 can be injected with the mixture of GnRH agonist (2.5 mg GnRH agonist, 110 mg methyl cellulose and 50 mg EVA), the Portal No. 2 can be injected with the mixture of estradiol (3 mg of estradiol and 300 mg of EVA), the Portal No. 3 can be injected with the progesterone mix (630 mg of progesterone and 1 g of EVA) and the Portal No. 4 can be injected with 500 mg of EVA (neat).

Example 9

Delayed Release Ring

The rate of hydration of the intravaginal device depends on many factors, including the rate of water penetration into the polymer. The rate of water penetration can be modulated by the osmotic pressure within the polymer. The osmotic pressure can be modulated by adding salt (NaCl, KCl, etc) to the formulation of the drug.

Estradiol and GnRH can be formulated as described herein. Yet, additional salt is added (300 mmol). These two drugs can form 2 segments of the ring and be designed to be release over 28 days (Table III). A third segment can incorporate Progesterone without salt (Table IV).

TABLE III

| Drug | Drug Circulation Level | Release from the Ring per day | Drug Loading for 28 days of Release |
|---|---|---|---|
| Estradiol | 100 pg/Ml | 100 μg | 3 mg |
| D-Trp6-Pro9-Net-GnRH | 10-100 pg/Ml | 4 μg/Kg = 240 μg/day | 6.8 mg |

TABLE IV

| Drug | Circulation | Release from the Ring per day | Drug Loading for 14 days of Release |
|---|---|---|---|
| Progesterone | 6 ng/mL | 45 mg | 630 mg |

As a result of the additional salt in the Estradiol and the GnRH agonist segments, these drugs will rehydrate sooner and immediately start their release which will continue over 28 days. However, the segment containing progesterone will begin the release after 14 days and continue for 4 days. Thus, a single ring may be used as birth control for about one month with an early phase of 2 weeks with a zero order release of just estradiol ("E2") and GnRH agonist, followed by 14 days of a zero order release of E2, GnRH agonist and progesterone.

All patents, patent applications, and published references cited herein are hereby incorporated by reference in their entireties. While this invention has been particularly shown and described with references to preferred embodiments thereof, it will be understood by those skilled in the art that various changes in form and details may be made therein without departing from the scope of the invention encompassed by the appended claims.

We claim:

1. A drug delivery system for the simultaneous release of a drug from two or more segments, comprising:
an implantable ring-shaped body comprising two or more arc-shaped segments having terminal ends mated to one another, at least two of the two or more segments being a homogenous mixture of a drug-permeable polymeric substance comprising ethylene-vinyl acetate copolymer and a drug such that the at least two segments are configured to release the drug at a substantially zero-order rate, wherein each segment has no membrane and is exposed on all sides of an outer surface extending between the terminal ends of the segment.

2. The drug delivery system of claim 1, wherein at least two of the segments comprise a different drug.

3. The drug delivery system of claim 1, wherein the drug is a hormone replacement steroid.

4. The drug delivery system of claim 1, wherein the drug is a contraceptive agent.

5. The drug delivery system of claim 1, wherein the drug is selected from the group consisting of: interferon, anti-angiogenesis factors, growth factors, hormones, enzymes, transferases, hydrolases, lysases, isomerases, proteases, ligases and oxidoreductases, enzyme inhibitors, steroids, anti-cancer drugs and antibiotics.

6. The drug delivery system of claim 1, wherein the drug is selected from the group consisting of: growth hormone, polysaccharides, antigens, and antibodies.

7. A drug delivery system, comprising:
an implantable body having a plurality of segments, each segment having first and second terminal ends that are each coupled to a terminal end of an adjacent segment, at least two of the segments being a homogenous mixture of a drug-permeable polymeric substance comprising ethylene-vinyl acetate copolymer and a drug such that the at least two segments are configured to release the drug at a substantially zero-order rate, and wherein each of the at least two segments has no membrane and is exposed on all sides 360° around a perimeter thereof to allow for release of the drug in all directions therefrom.

exposed on all sides 360° around a perimeter thereof to allow for release of the drug in all directions therefrom.

8. The drug delivery system of claim 7, wherein each segment has a cross-sectional diameter substantially identical to a cross-sectional diameter of the implantable body.

9. The drug delivery system of claim 7, wherein the implantable body is ring-shaped, and each segment comprises an arc of the ring.

* * * * *

```
SEQUENCE LISTING

<160> NUMBER OF SEQ ID NOS: 1

<210> SEQ ID NO 1
<211> LENGTH: 10
<212> TYPE: PRT
<213> ORGANISM: Unknown
<220> FEATURE:
<223> OTHER INFORMATION: Synthetic Peptide Sequence

<400> SEQUENCE: 1

Glu His Trp Ser Tyr Gly Leu Arg Pro Gly
1               5                   10
```